(12) United States Patent
Stanton et al.

(10) Patent No.: US 7,223,543 B2
(45) Date of Patent: May 29, 2007

(54) CONJUGATED LINOLEIC ACID ISOMERASE AND A PROCESS FOR THE PRODUCTION OF CONJUGATED LINOLEIC ACID

(75) Inventors: Catherine Stanton, Fermoy (IE); R. Paul Ross, Fermoy (IE); Oskar Zelder, Speyer (DE); Bruno Kaesler, Ludwigshafen (DE)

(73) Assignee: Teagasc Dairy Products Research Centre (IE)

( * ) Notice: Subject to any disclaimer, the term of this patent is extended or adjusted under 35 U.S.C. 154(b) by 0 days.

(21) Appl. No.: 10/480,121

(22) PCT Filed: Jun. 10, 2002

(86) PCT No.: PCT/EP02/06341

§ 371 (c)(1),
(2), (4) Date: Dec. 5, 2003

(87) PCT Pub. No.: WO02/101056

PCT Pub. Date: Dec. 19, 2002

(65) Prior Publication Data

US 2004/0197790 A1   Oct. 7, 2004

(30) Foreign Application Priority Data

Jun. 8, 2001   (EP) .................................. 01113962

(51) Int. Cl.
*C12Q 1/68*   (2006.01)
*C07F 9/02*   (2006.01)
*C12P 7/64*   (2006.01)

(52) U.S. Cl. ................. 435/6; 435/134; 435/252.3; 435/388.4; 435/69.1

(58) Field of Classification Search ........... 435/6, 435/134, 252.3, 388.4, 69.1; 530/388.4
See application file for complete search history.

(56) References Cited

U.S. PATENT DOCUMENTS

| 3,356,699 A | 12/1967 | Bagby et al. |
| 4,164,505 A | 8/1979 | Krajca |
| 5,922,375 A | 7/1999 | Luchansky et al. |
| 6,706,501 B1 * | 3/2004 | Rosson et al. ............. 435/134 |

FOREIGN PATENT DOCUMENTS

| EP | 1227152 A1 | 7/2002 |
| EP | 1264893 A1 | 12/2002 |
| WO | WO-94/16690 A1 | 8/1994 |
| WO | WO-96/06605 A1 | 3/1996 |
| WO | WO-97/32008 A1 | 9/1997 |
| WO | WO-97/46118 A1 | 12/1997 |
| WO | WO-97/46230 A1 | 12/1997 |
| WO | WO-99/29886 A1 | 6/1999 |
| WO | WO-99/32604 A1 | 7/1999 |
| WO | WO-00/42168 A2 | 7/2000 |
| WO | WO-01/58465 A2 | 8/2001 |
| WO | WO-02/38798 A1 | 5/2002 |
| WO | WO-02/101056 A3 | 12/2002 |

OTHER PUBLICATIONS

WO 02/074798 Fabrizio et al. The genome of Bifidobacterium Jan. 30, 2002.*
WO 99/29886 Bjorck et al. Formation of conjugated unsaturated fatty acids.*
Banni, Sebastiano, et al., "Decrease in linoleic acid metabolites as a potential mechanism in cancer risk reduction by conjugated linoleic acid," *Carcinogenesis*, vol. 20(6):1019-1024 (1999).
Biavati, B., et al., "Bifidobacteria: history, ecology, physiology and applications," *Annals of Microbiology*, vol. 50:117-131 (2000).
Booth, Roland Gordon, et al., "A Study of Seasonal Variation in Butter Fat. II. A Seasonal Spectroscopic Variation in the Fatty Acid Fraction," *Biochem. J.*, vol. 29:133-137 (2000).
Charteris, William P., et al., "Selective detection, enumeration and identification of potentially probiotic *Lactobacillus* and Bifidobacterium species in mixed bacterial populations," *International Journal of Food Microbiology*, vol. 35:1-27 (1997).
Chin, Sou F., et al., "Conjugated Linoleic Acid (9, 11-and 10, 12-Octadecadienoic Acid) Is Produced in Conventional but Not Germ-Free Rats Fed Linoleic Acid," *J. Nutr.*, vol. 124(5):694-701 (1994).
Chin, S.F., et al., "Dietary Sources of Conjugated Dienoic Isomers of Linoleic Acid, a Newly Recognized Class of Anticarcinogens," *Journal of Food Composition and Analysis*, vol. 5:185-197 (1992).
Dunne, Colum, et al., "Probiotics: from myth to reality. Demonstration of functionality in animal models of disease and in human clinical trials," *Antonie Van Leeuwenhoek*, vol. 76:279-292 (1999).
Feng, Da-Fei, et al., "Progressive Sequence Alignment as a Prerequisite to Correct Phylogenetic Trees," *Journal of Molecular Evolution*, vol. 25:351-360 (1987).
Fritsche, Jan, et al., "Amounts of conjugated linoleic acid (CLA) in German foods and evalution of daily intake," *Z Lebensm Unters Forsch A*, vol. 206:77-82 (1998).
Fritsche, Han, et al., "Conjugated linoleic acid (CLA) isomers in human adipose tissue," *Z Lebensm Unters Forsch A*, vol. 205:415-418 (1997).
Fritsche, Jan, et al., "Analysis, occurance, and physiological properties of trans fatty acids (TFA) with particular emphasis on conjugated linoleic acid isomers (CLA)—a review," *Fett/Lipid*, vol. 100:190-210 (1998).

(Continued)

*Primary Examiner*—Ponnathapura Achutamurthy
*Assistant Examiner*—Kagnew Gebreyesus
(74) *Attorney, Agent, or Firm*—Lahive & Cockfield, LLP; Elizabeth A. Hanley; Maria Laccotripe Zacharakis

(57) ABSTRACT

The present invention relates to a process for the production of conjugated linoleic acid and a process for the production of triglycerides with an increased content of conjugated linoleic acid. Moreover, the invention relates to a nucleic acid sequence; a nucleic acid construct, a vector and transgenic organisms comprising at least one nucleic acid sequence or one nucleic acid construct which encodes a polypeptide with conjugated linoleic isomerase activity. Furthermore, the invention relates to the use of a microorganism of the genus *Bifidobacterium* as a probiotic.

17 Claims, 12 Drawing Sheets

OTHER PUBLICATIONS

Herbel, Barbara K., et al., "Safflower oil consumption does not increase plasma conjugated linoleic acid concentrations in humans," *Am. J. Clin. Nutr.*, vol. 67:332-337 (1998).

Higgins, Desmond G., et al., "Fast and sensitive multiple sequence alignments on a microcomputer," *Comput. Appl. Biosci.*, vol. 5(2):151-153 (1989).

Huang, Yi-Chia, et al., "Effect of Cheddar Cheese Consumption on Plasma Conjugated Linoleic Acid Concentrations in Men," *Nutrition Research*, vol. 14(3):373-386 (1994).

Ip, Clement, et al., "Effect of Timing and Duration on Dietary Conjugated Linoleic Acid on Mammary Cancer Prevention," *Nutr. Cancer.*, vol. 24(3):241-7 (1995).

Jiang, J., et al., "Production of conjugated linoleic acid by dairy starter culture," *Journal of Applied Microbiology*, vol. 85:95-102 (1998).

Jiang, J., et al., "Relation between the intake of milk fat and the occurence of conjugated linoleic acid in human adipose tissue," *Am. J. Clin. Nutr.*, vol. 70:21-7 (1999).

Kailasapathy, Kaila, et al., "Survival and therapeutic potential of probiotic organisms with reference to *Lactobacilius acidophilus* and *Bifidobacterium* spp.," *Immunology and Cell Biology*, vol. 78:80-88 (2000).

Kepler, C.R., et al., "Linoleate$\Delta^{12}$-cis, $\Delta^{11}$-trans-Isomerase," *Enzymology. Lipids.*, Academic Press XIV, New York, London, pp. 105-109 (1969).

Kepler, Carol R., et al., "Biohydrogenation of Unsaturated Fatty Acids. IV. Substrate Specificity and Inhibition of Linoleate $\Delta^{12}$-cis, $\Delta^{11}$-trans-Isomerase from Butyrivibrio Fibrisolvens," *The Journal of Biological Chemistry*, vol. 245(14):3612-3620 (1970).

Kepler, Carol R., et al., "Biohydrogenation of Unsaturated Fatty Acids. V. Stereospecificity of Proton Addition and Mechanism of Action of Linoleic Acid $\Delta^{12}$-cis, $\Delta^{11}$-trans-Isomerase from Bityrivibrio Fibrisolvens," *The Journal of Biological Chemistry*, vol. 246(9):2765-71 (1971).

McGuire, Michelle K., et al., "Dietary Sources and Intakes of Conjugated Linoleic Acid Intake in Humans," *The World's Knowledge*, Chapter 29, pp. 369-377.

Salminen, Irma, et al., "Dietary trans fatty acids increase conjugated linoleic acid levels in human serum," *Nutritional Biochemistry*, vol. 9:93-98 (1998).

Scardovi, Vittorio, "The Prokaryotes, A Handbook on Habitats, Isolation, and Identification of Bacteria, vol. II," Chapter 149, pp. 1951-1957 (1981).

Thompson, Henry, et al., "Morphological and Biochemical Status of the Mammary Gland as Influenced by Conjugated Linoleic Acid: Implication for a Reduction in Mammary Cancer Risk," *Cancer Research*, vol. 57:5067-5072 (1997).

\* cited by examiner

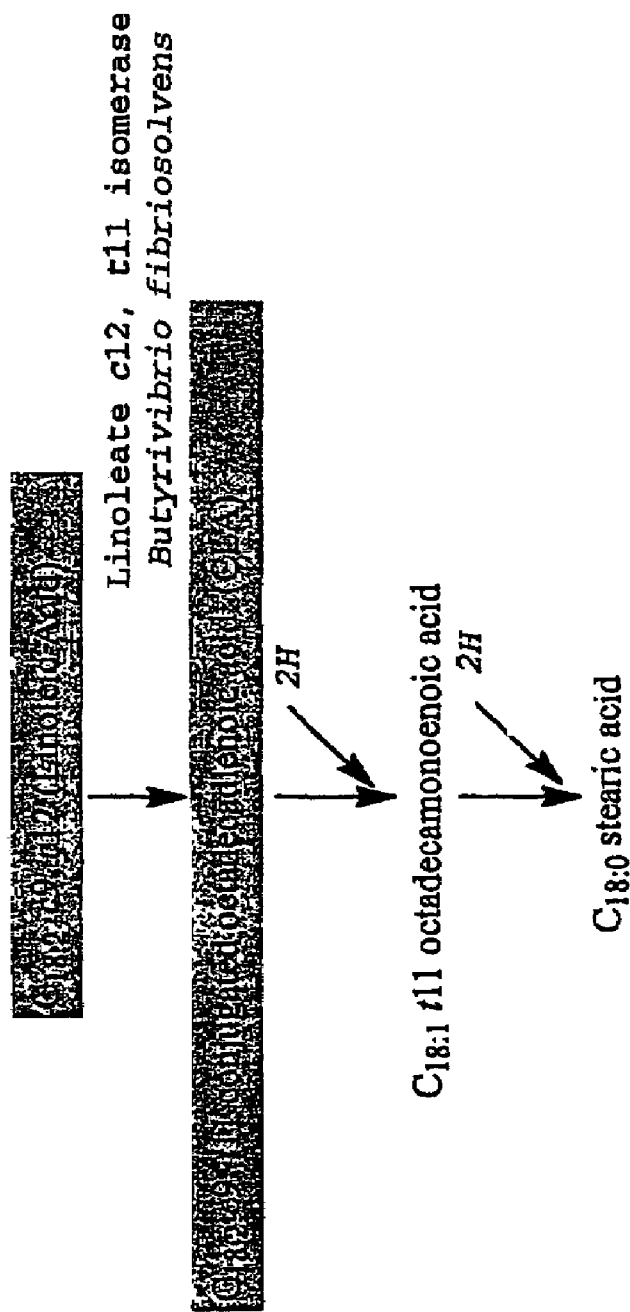
Figur 1: Biohydrogenation of linoleic acid in the rumen.

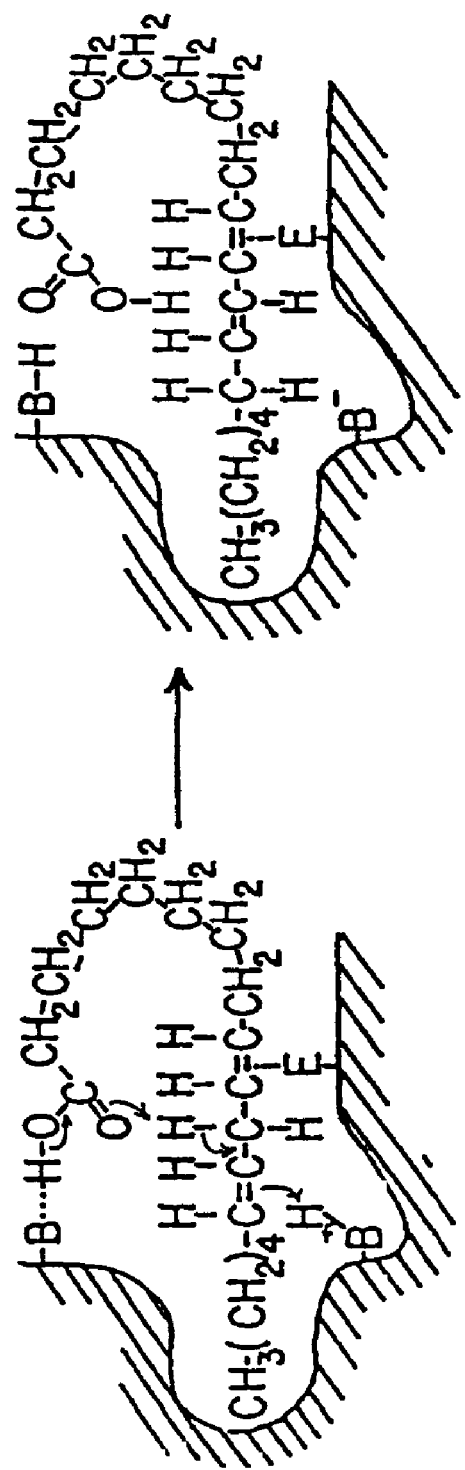
Figur 2: Proposed model for the isomerization of linoleic acid isomerase

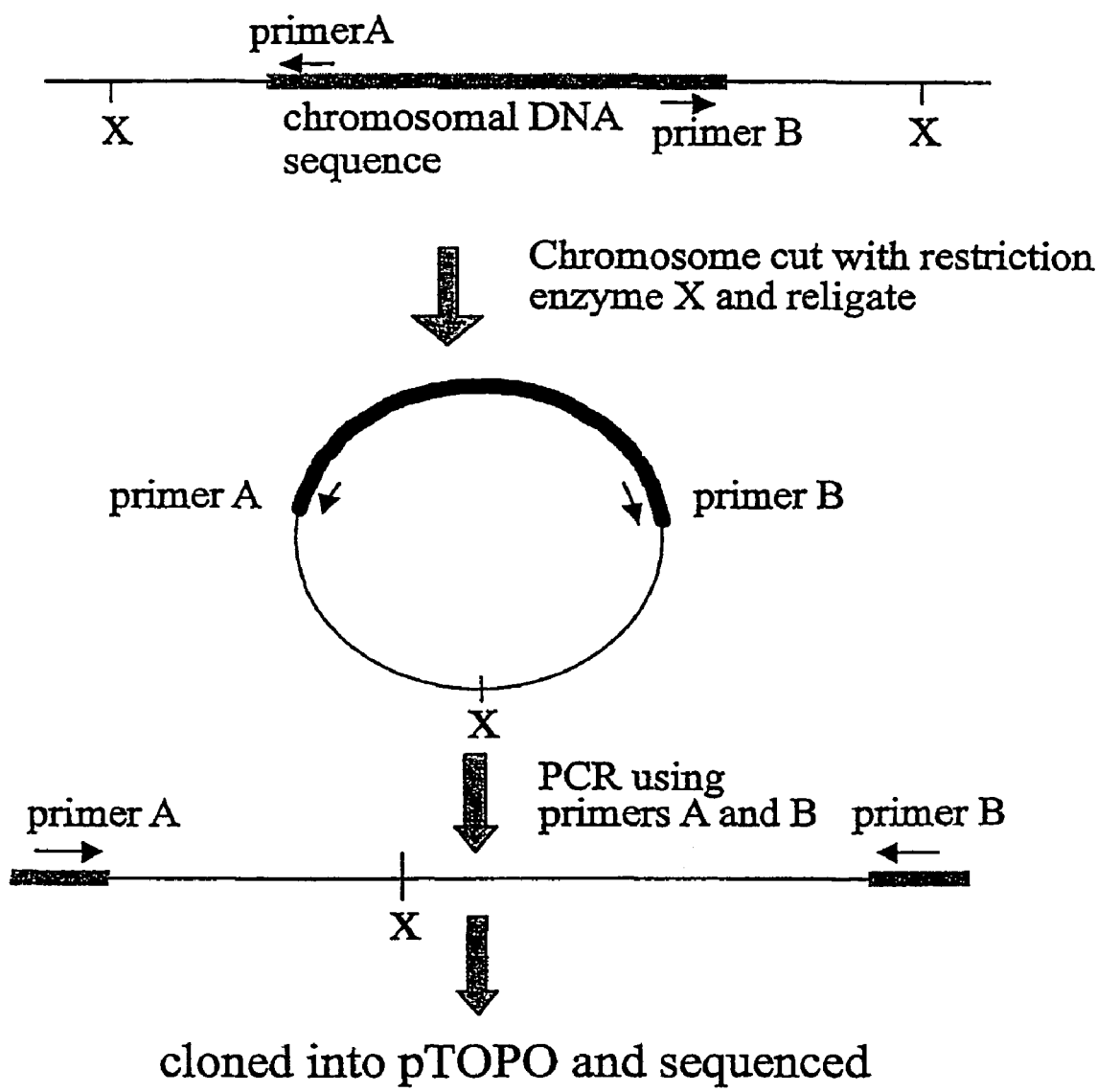
Figur 3: Method for chromosomal walking by inverse PCR

Figur 4: Map of pCR®2.1-TOPO®
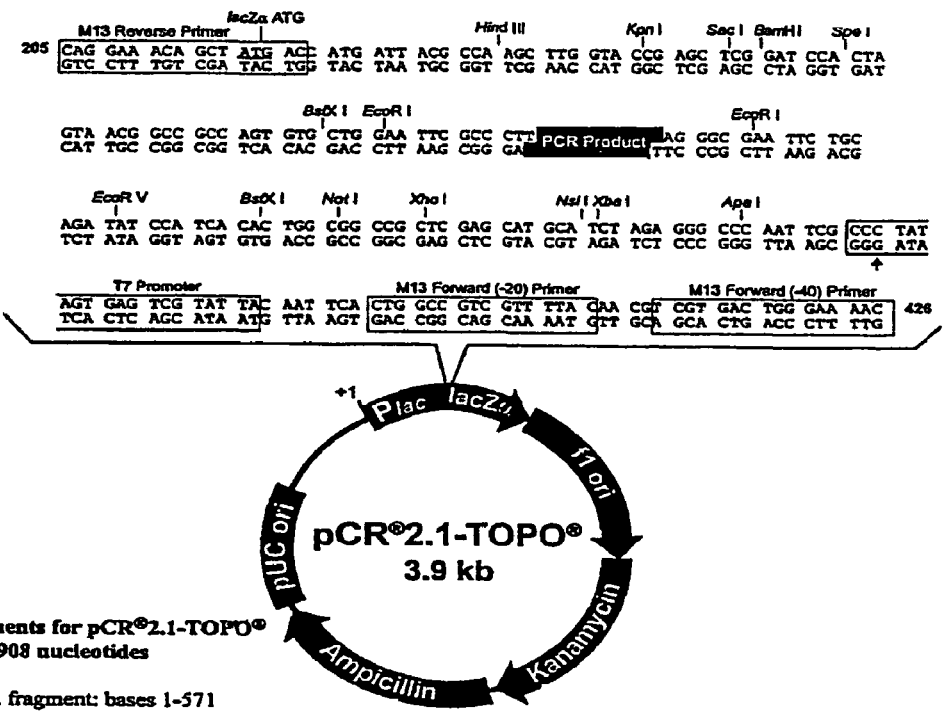

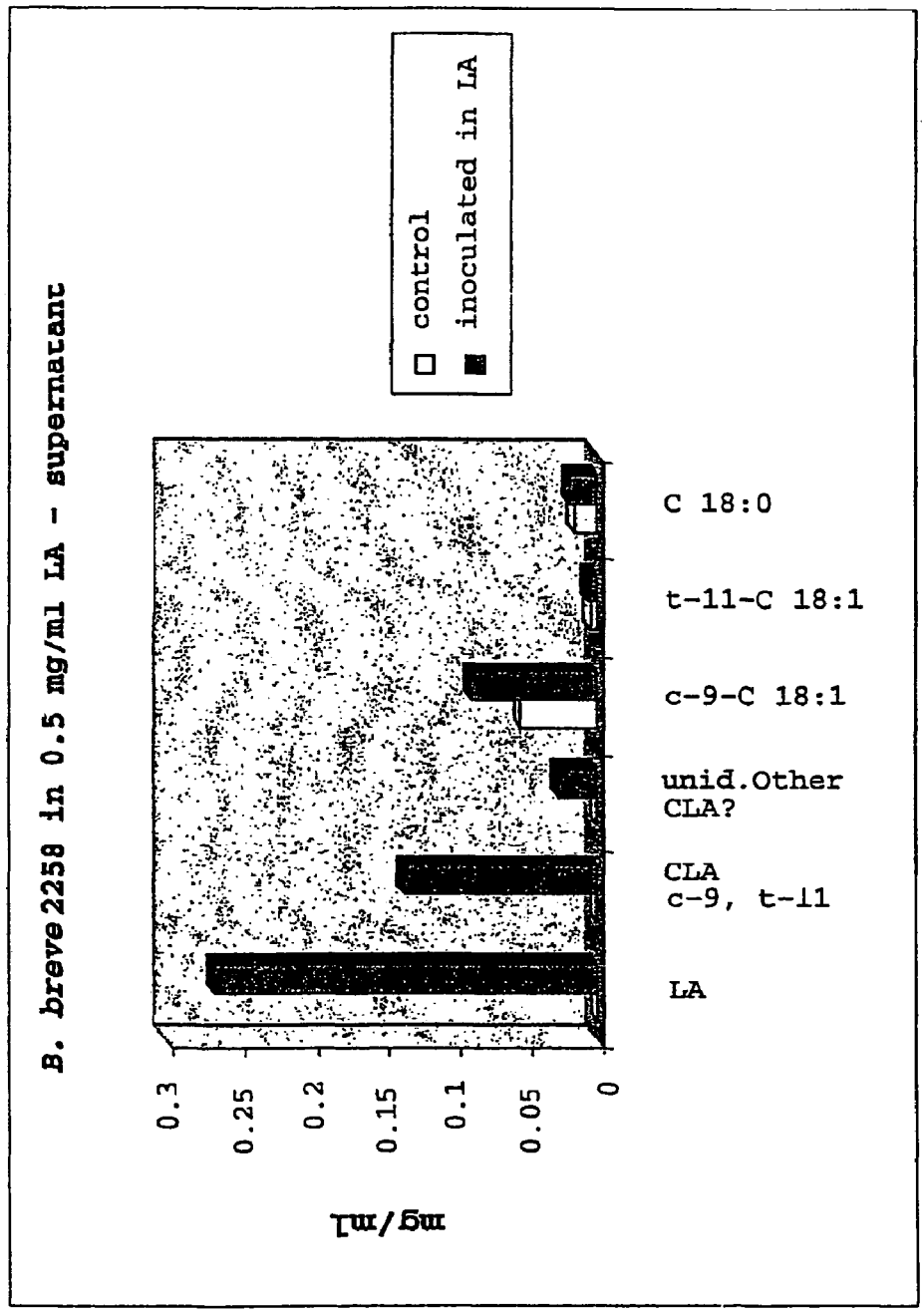
Fig. 5. Fatty acid composition of supernatant following incubation in MRS medium containing 0.5 mg/ml LA with *B. breve* 2258 incubated in MRS medium alone.

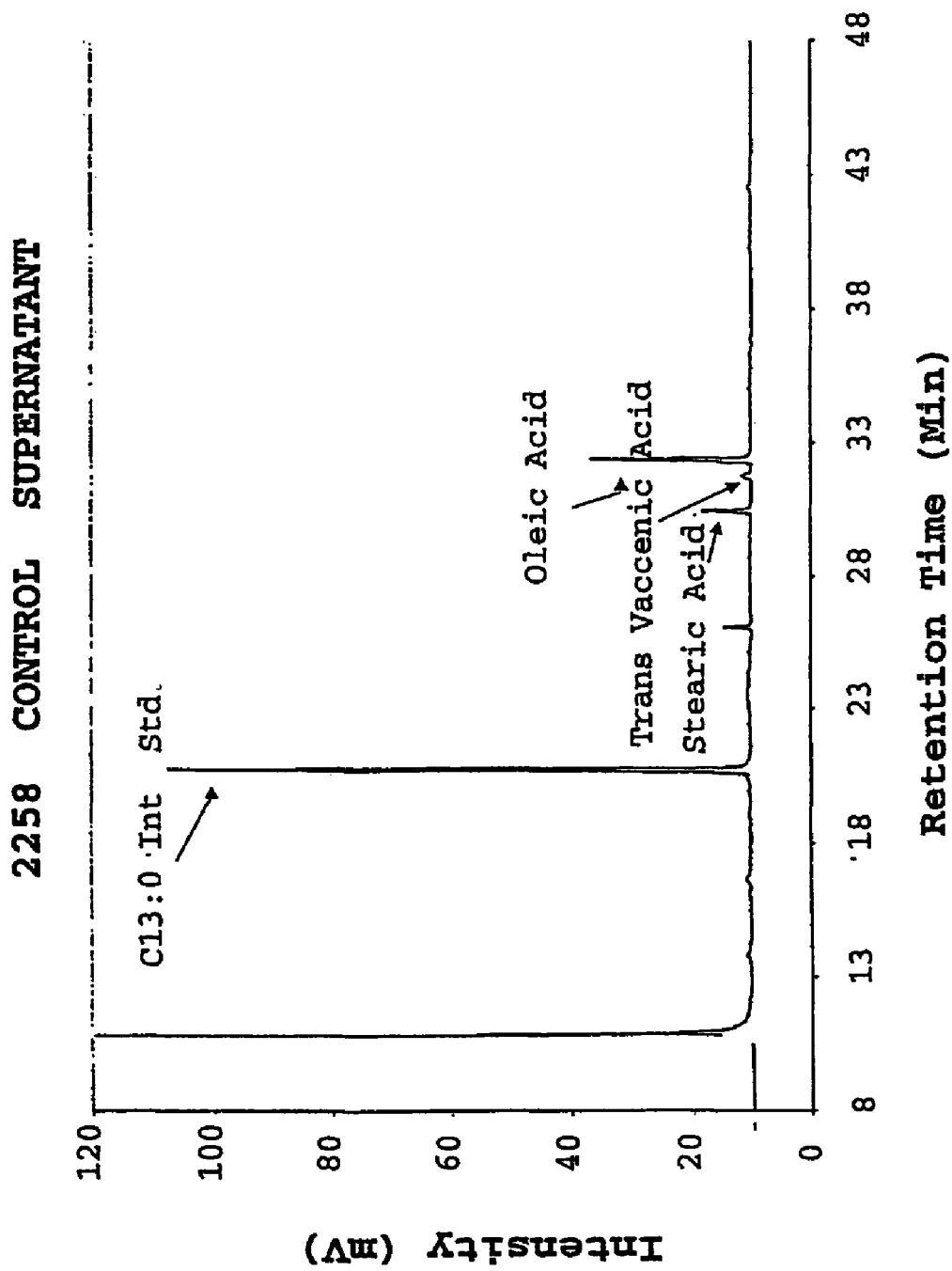
Fig. 6. GLC chromatogram of *B. breve* 2258, control supernatant.

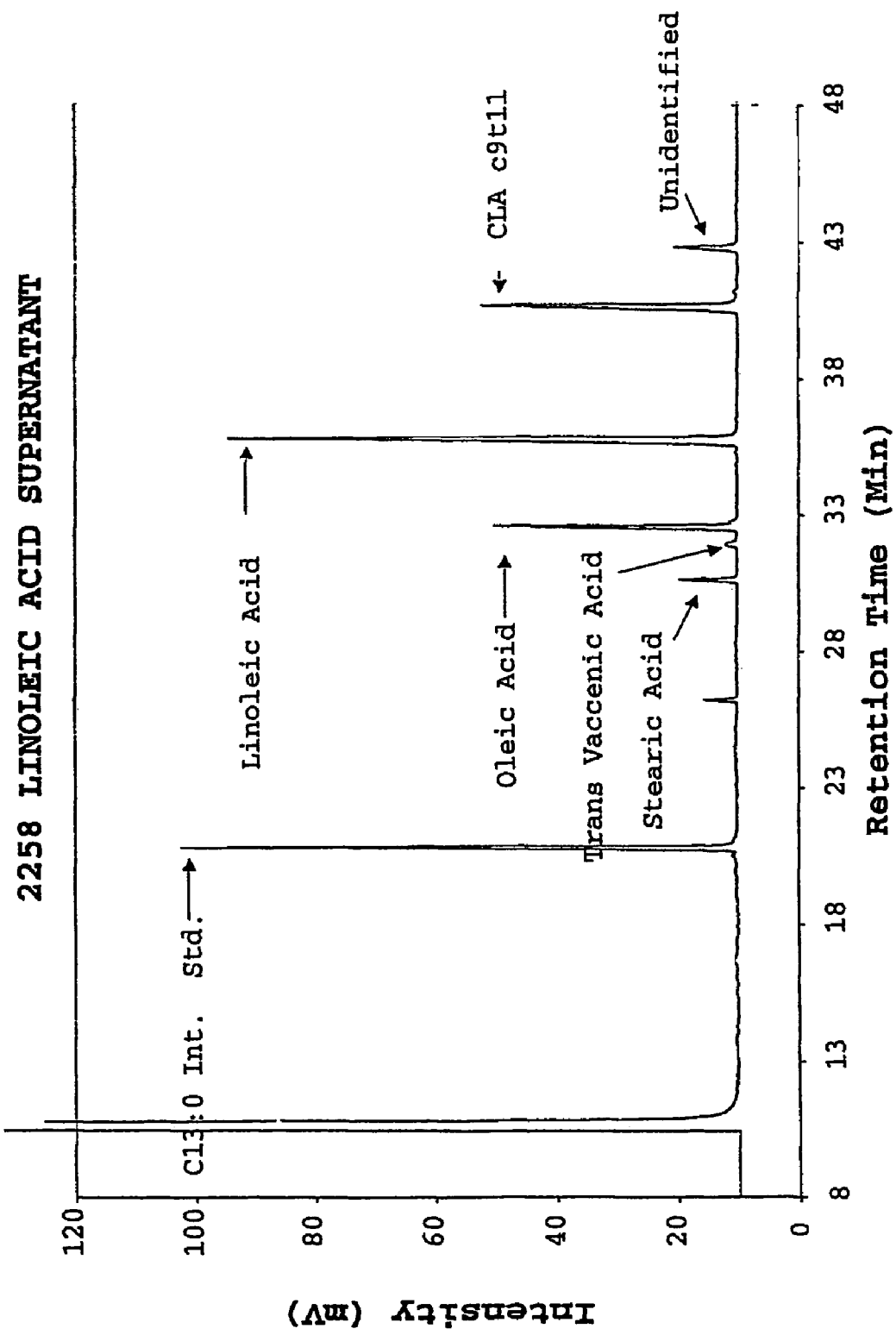
Fig. 7. GLC chromatogram of *B. breve* 2258, added LA supernatant.

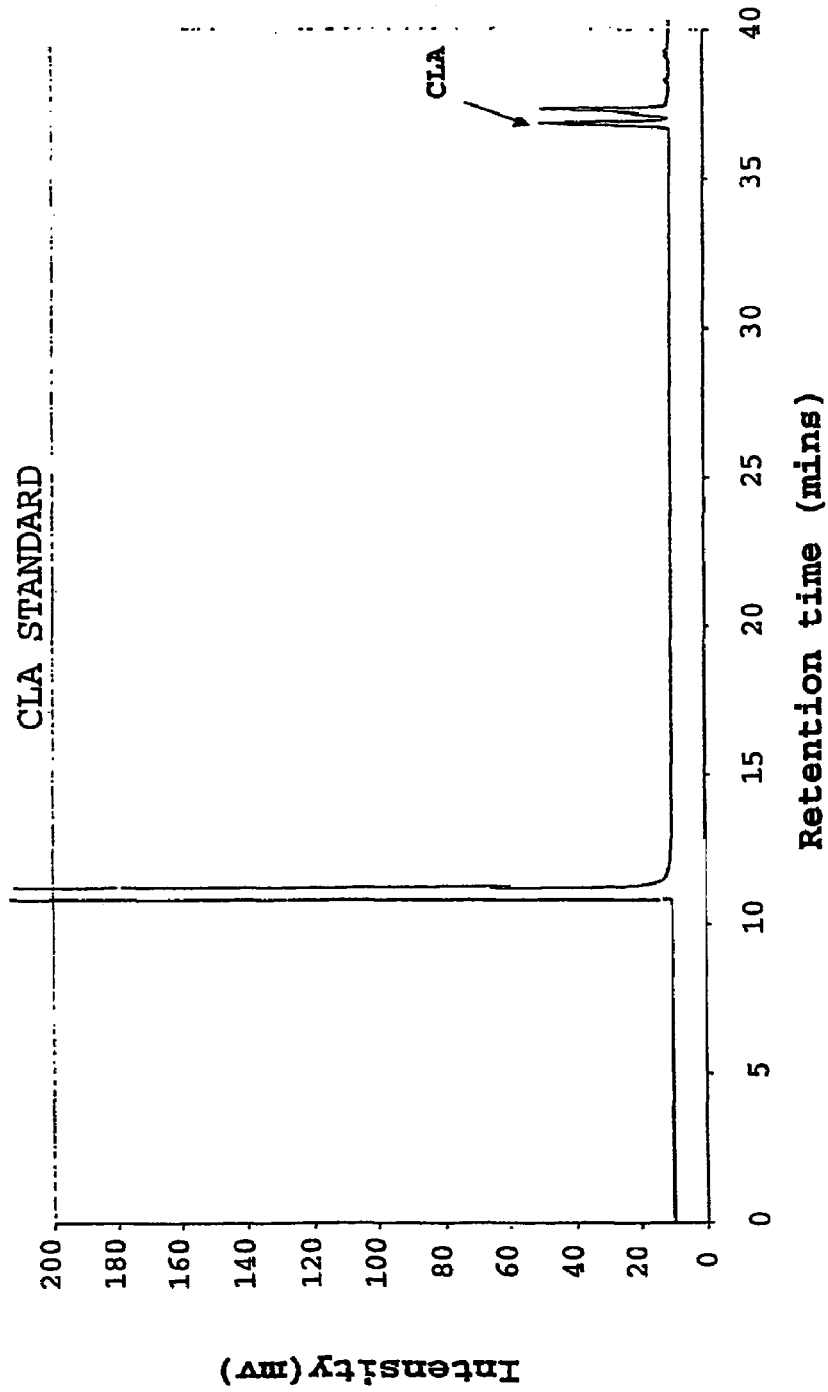
Fig. 8. Chromatogram of CLA standard (Nu-Chek-Prep. Inc. Elysian MN). Separation was performed on Chrompack CP Sil 88 column (Chrompack, Middleburg, The Netherlands) (60 m x 0.25 mm i.d., 0.20 m film thickness). The retention time on this column is different from the column used for the bacterial fatty acids.

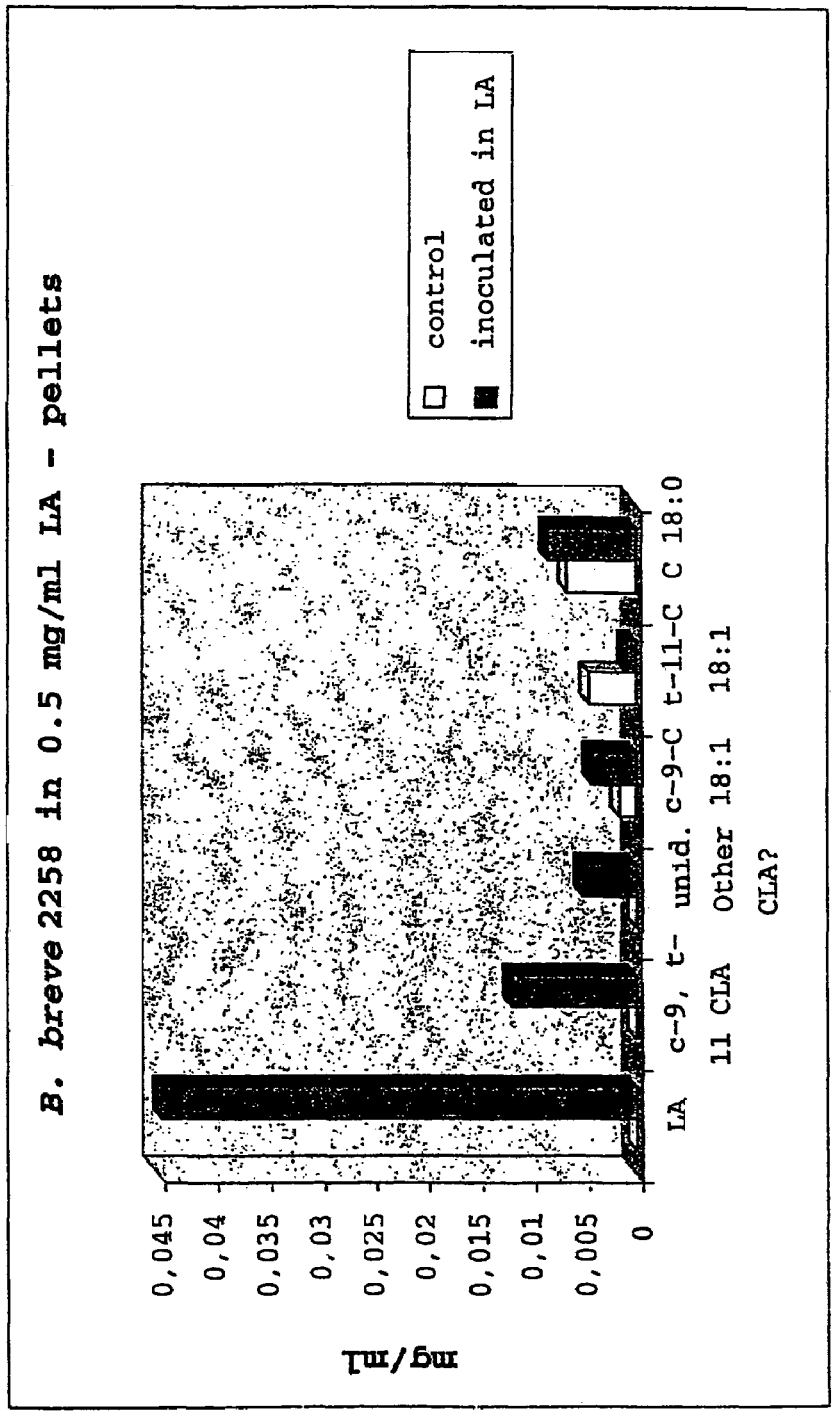
Fig. 9. Fatty acid composition of pellets following incubation in MRS medium containing 0.5 mg/ml LA with *B. breve* 2258 for 24 h. The control was *B. breve* 2258 incubated in MRS medium alone.

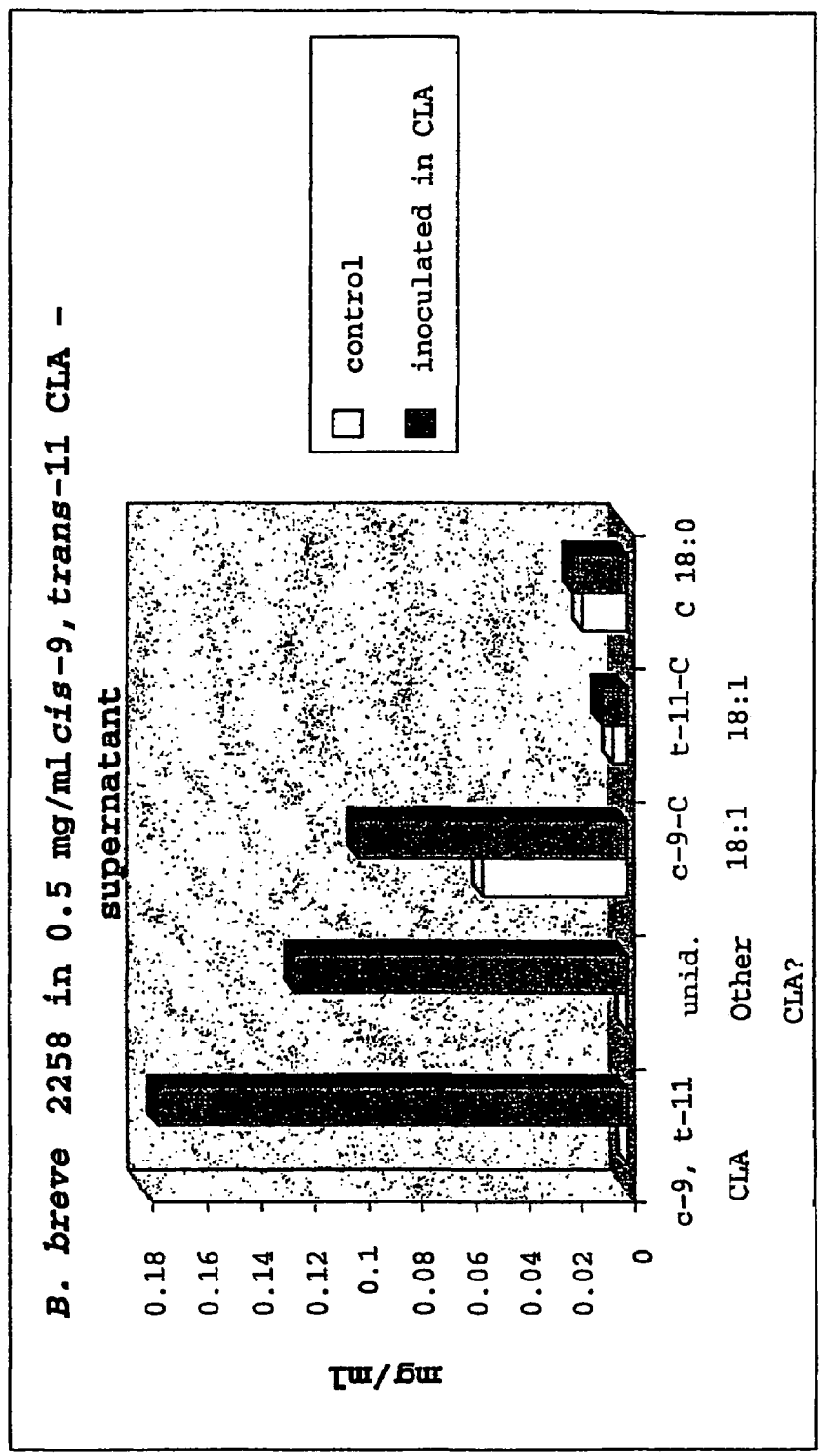
Fig. 10. Fatty acid composition of supernatant following incubation in MRS medium containing 0.5 mg/ml cis-9, trans-11 CLA with B. breve 2258 for 48 h. The control was B. breve 2258 incubated in MRS medium alone.

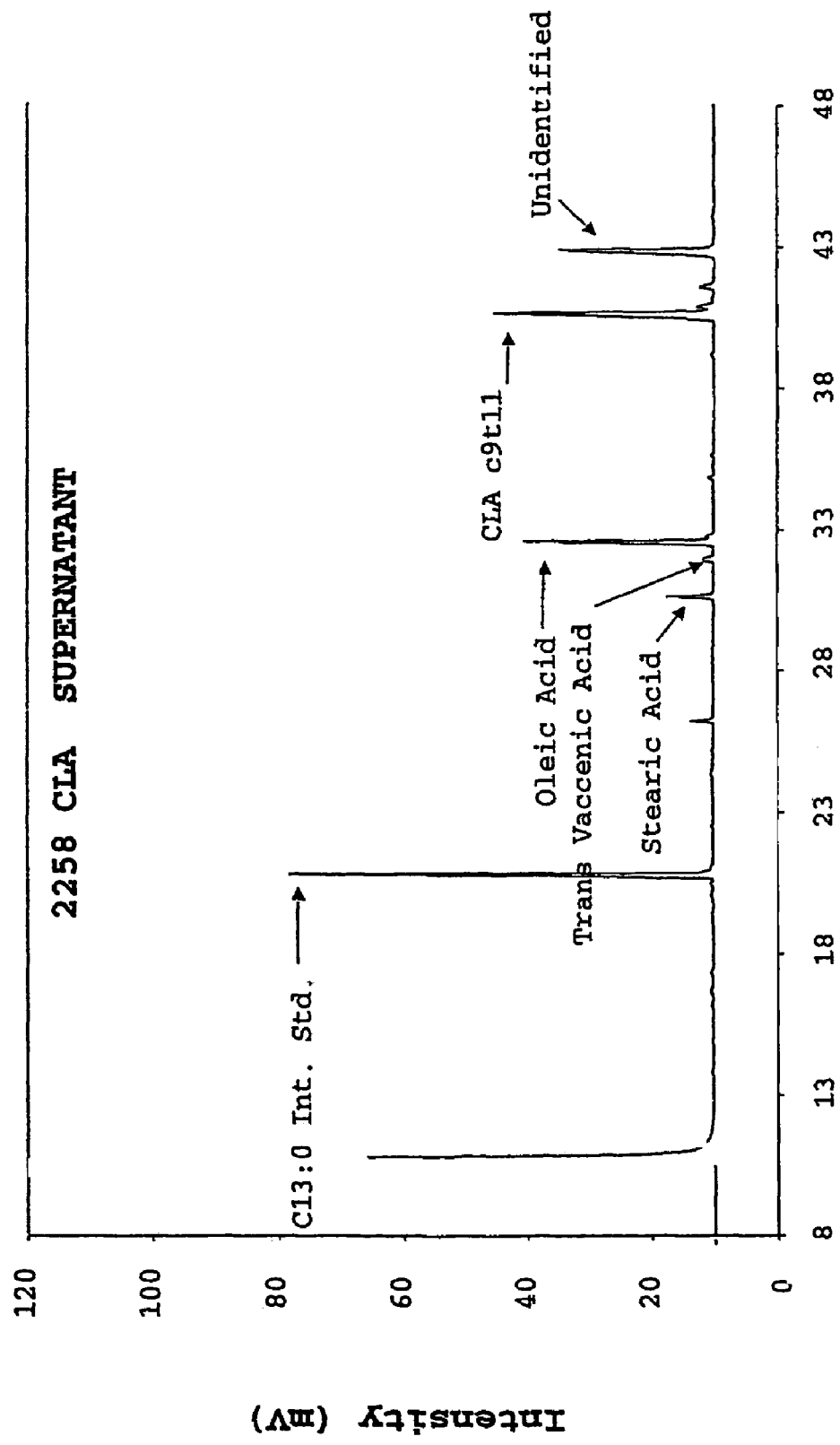
Fig. 11. GLC chromatogram of B. breve 2258, added CLA supernatant.

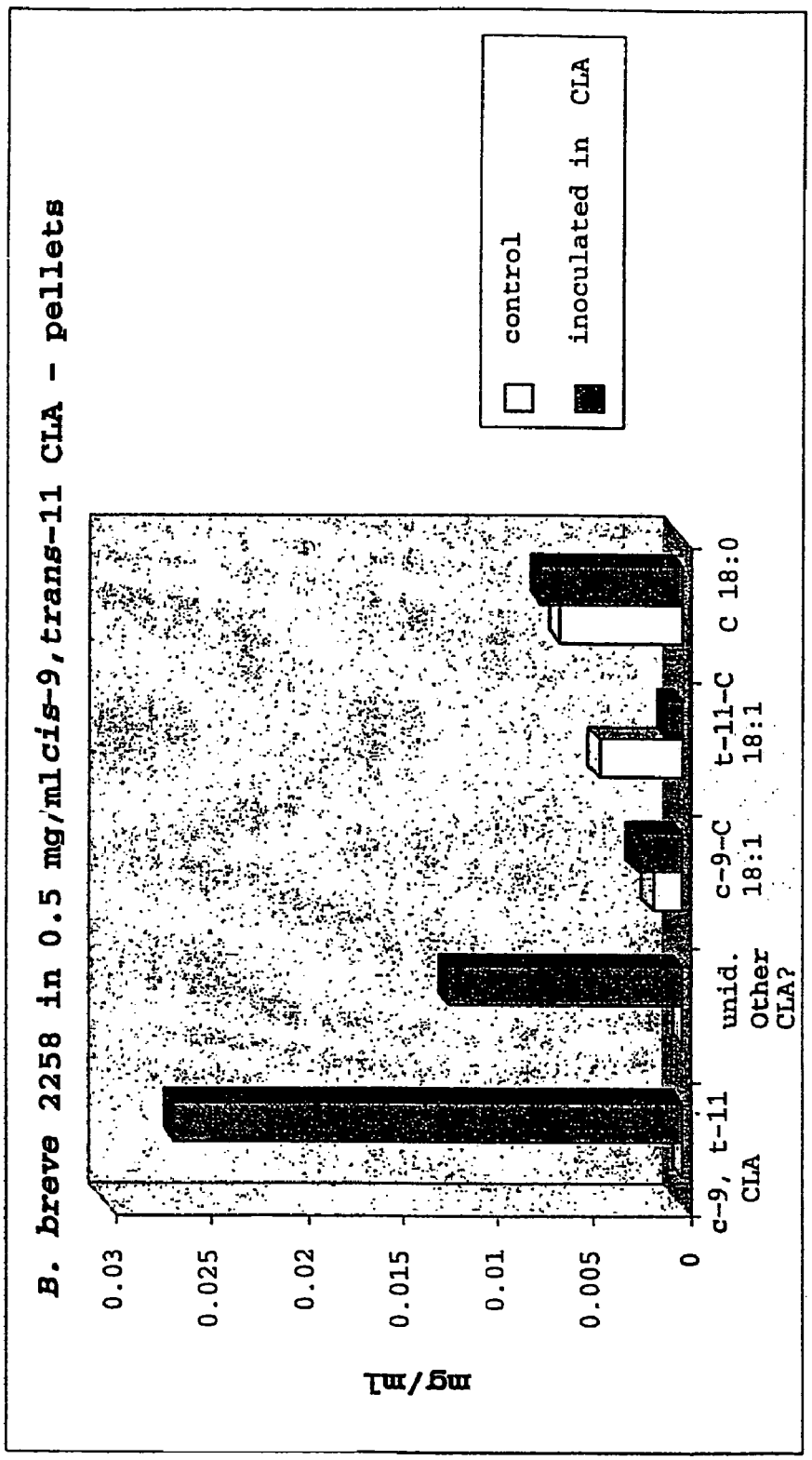
Fig. 12. Fatty acid composition of pellets following incubation in MRS medium containing 0.5 mg/ml cis-9, trans-11 CLA with *B. breve* 2258 for 48 h. The control was *B. breve* 2258 incubated in MRS medium alone.

SEQUENCE LISTING

<160> NUMBER OF SEQ ID NOS: 2

<210> SEQ ID NO 1
<211> LENGTH: 1985
<212> TYPE: DNA
<213> ORGANISM: Bifidobacterium breve

<400> SEQUENCE: 1

```
aactgcagtg gattgtcaat tcatccccaa ggaggcggaa c atg tac tac agc agc         56 ggc aac tat gag gcg ttt gcc cgt ccg aag aag cca gcc ggc gta gac          104 agc aag cat gca tat atc atc ggc acc ggt ctg gcg gcc ttg tct tcg          152 gcc tgt tac ctg gtg cgt gac ggc cag atg cca ggc gat cat att cat          200 att ctc gaa aag gat ccc gta ccg gga gga gcc tgc gat ggt ctc gat          248 att cct ggt ctc ggt tat gtg atg cgc ggc ggc cgc gaa atg gac aat          296 cat ttc gag gtc atg tgg gat ctc ttc cgt tcg att ccc tcc atc gag          344 acc gag gga gtc agc gtg ctc gac gaa tac tat tgg ctc aac aag gaa          392 gat ccg aat tac tcg cta tgc cgc gcc acc aaa gat ctc ggc aag gat          440 gcc gga ctc aag ggc aaa ttc gga ttg tct gac aag gct tcc atg gaa          488 atc atg aag ctg ttc ttc act ccg gac gag gac ctg tat gac aag ccg          536 atc acc gat ttc ttc gat gac gag gtg ctg aac tcc aac ttc tgg ctg          584 tac tgg cgt acc atg ttc gct ttt gaa aat tgg cat tca gcg ttg gaa          632 atg aag ctg tac atc aag cgc tac att cat cac atc ggc ggc ttg ccg          680 gac ttc tcc gca ctg cga ttc acc cgc tac aac cag tac gag tcg atg          728 att ttg ccc atg gtc aaa tat ctg gaa tct cat ggc gtg gaa ttc cga          776 tac aac acc aag gtc gag aac gtc gaa ttc gcc atc ggt ggg gga gac          824 ggc ccc aag cgc gag cat act ggc gtc gga caa gac acc atc cag aaa          872 atc cag gcc act tcc ggt ttc ttc aag cgc aat cca gcc agc acc ccc          920 acc aag aag ctc gcc gta cgc atc gat gtc agc cag gaa ggg gag aag          968 tcc tct atc gat ctg acg gaa aac gat ctg gtg ttc atc acc aac ggc         1016 ggc tgc gtg gag aac tcc act atg ggt tcg cag aat tcg ccc gcc gca         1064 tgg aat ccg gat ctg aag cca ggc ggc ggc tgg gat atg tgg agg cgt         1112 atc gcc gaa cag gat ccg agc ttc ggt cat ccg gaa aag ttc tgt tcc         1160 gac ccg aac gcc acc aag tgg atg agc gcc act gtt acc act ttg gac         1208 gat gag att cct ccg tat att cag aag ata tgc aag cgc gat ccg ttc         1256 tcc ggc aag gty gtc acc ggc ggc atc gtc act gtg cag gat tct aac         1304 tgg ctg atg agc tgg acg ctc aat cgt caa cag cag ttc cgc gat cag         1352
```

-continued

```
ccc aag gat cag ctg tgc gta tgg gtc tat ggc ctg ttc ccg gac aag      1400 ccg ggc aac tat gtg aag aag ccg atg acc gaa tgc acc ggc gag gag      1448 atc tgt gag gag tgg ctc tac cac atg ggc gta ccg acc gac aag atc      1496 gag tcg ctt gcc aaa cat cat gcc aat acc gtg ccg gtg atg atg cca      1544 tac atc act gca ttc ttc atg cct cgc gca gcc ggc gwc cgc ccg gac      1592 gtg gtr ccc gat ggc gcc gtg aac ttc gca ttc ctc ggc cag ttc gcc      1640 gaa acc cca cgc gay acs rtc ttc acc acc gaa tay tcg atg cgt acc      1688 ggt atg gaa gcc gtc tat acg ctg ctc ggg gtg gat cgt ggc gtg ccc      1736 gag gtg tgg ggc agc gtc tat gac gtg cgc aac ctg ctc aac gcc acc      1784 gtc aaa ctg cgt gac ggc gca ccg gtg acg gat atg aag ctc aac ttc      1832 att gaa rag gcc gtg gtc aag aag gtg ctt aag aag ctc gat ggc acg      1880 gat att gct acc ctg cta cgc gra tac cat gtg atc tgaattgatt           1926 cggctcccgt tccgccctgt gcgggaggga gccgttcgca taatcgggca agcttgggg     1985
```

<210> SEQ ID NO 2
<211> LENGTH: 624
<212> TYPE: PRT
<213> ORGANISM: Bifidobacterium breve
<220> FEATURE:
<221> NAME/KEY: VARIANT
<222> LOCATION: 514
<223> OTHER INFORMATION: Xaa = Asp or Val
<220> FEATURE:
<221> NAME/KEY: VARIANT
<222> LOCATION: 540
<223> OTHER INFORMATION: Xaa= Ile or Val
<220> FEATURE:
<221> NAME/KEY: VARIANT
<222> LOCATION: 600
<223> OTHER INFORMATION: Xaa=Lys or Glu
<220> FEATURE:
<221> NAME/KEY: VARIANT
<222> LOCATION: 621
<223> OTHER INFORMATION: Xaa=Glu or Gly

<400> SEQUENCE: 2

```
Met Tyr Tyr Ser Ser Gly Asn Tyr Glu Ala Phe Ala Arg Pro Lys Lys
 1               5                  10                  15

Pro Ala Gly Val Asp Ser Lys His Ala Tyr Ile Ile Gly Thr Gly Leu
            20                  25                  30

Ala Ala Leu Ser Ser Ala Cys Tyr Leu Val Arg Asp Gly Gln Met Pro
        35                  40                  45

Gly Asp His Ile His Ile Leu Glu Lys Asp Pro Val Pro Gly Gly Ala
    50                  55                  60

Cys Asp Gly Leu Asp Ile Pro Gly Leu Gly Tyr Val Met Arg Gly Gly
65                  70                  75                  80

Arg Glu Met Asp Asn His Phe Glu Val Met Trp Asp Leu Phe Arg Ser
                85                  90                  95

Ile Pro Ser Ile Glu Thr Glu Gly Val Ser Val Leu Asp Glu Tyr Tyr
            100                 105                 110

Trp Leu Asn Lys Glu Asp Pro Asn Tyr Ser Leu Cys Arg Ala Thr Lys
        115                 120                 125

Asp Leu Gly Lys Asp Ala Gly Leu Lys Gly Lys Phe Gly Leu Ser Asp
    130                 135                 140

Lys Ala Ser Met Glu Ile Met Lys Leu Phe Phe Thr Pro Asp Glu Asp
```

```
                145                 150                 155                 160
Leu Tyr Asp Lys Pro Ile Thr Asp Phe Phe Asp Asp Glu Val Leu Asn
                165                 170                 175
Ser Asn Phe Trp Leu Tyr Trp Arg Thr Met Phe Ala Phe Glu Asn Trp
                180                 185                 190
His Ser Ala Leu Glu Met Lys Leu Tyr Ile Lys Arg Tyr Ile His His
                195                 200                 205
Ile Gly Gly Leu Pro Asp Phe Ser Ala Leu Arg Phe Thr Arg Tyr Asn
                210                 215                 220
Gln Tyr Glu Ser Met Ile Leu Pro Met Val Lys Tyr Leu Glu Ser His
225                 230                 235                 240
Gly Val Glu Phe Arg Tyr Asn Thr Lys Val Glu Asn Val Glu Phe Ala
                245                 250                 255
Ile Gly Gly Gly Asp Gly Pro Lys Arg Glu His Thr Gly Val Gly Gln
                260                 265                 270
Asp Thr Ile Gln Lys Ile Gln Ala Thr Ser Gly Phe Phe Lys Arg Asn
                275                 280                 285
Pro Ala Ser Thr Pro Thr Lys Lys Leu Ala Val Arg Ile Asp Val Ser
                290                 295                 300
Gln Glu Gly Glu Lys Ser Ser Ile Asp Leu Thr Glu Asn Asp Leu Val
305                 310                 315                 320
Phe Ile Thr Asn Gly Gly Cys Val Glu Asn Ser Thr Met Gly Ser Gln
                325                 330                 335
Asn Ser Pro Ala Ala Trp Asn Pro Asp Leu Lys Pro Gly Gly Gly Trp
                340                 345                 350
Asp Met Trp Arg Arg Ile Ala Glu Gln Asp Pro Ser Phe Gly His Pro
                355                 360                 365
Glu Lys Phe Cys Ser Asp Pro Asn Ala Thr Lys Trp Met Ser Ala Thr
                370                 375                 380
Val Thr Thr Leu Asp Asp Glu Ile Pro Pro Tyr Ile Gln Lys Ile Cys
385                 390                 395                 400
Lys Arg Asp Pro Phe Ser Gly Lys Val Val Thr Gly Gly Ile Val Thr
                405                 410                 415
Val Gln Asp Ser Asn Trp Leu Met Ser Trp Thr Leu Asn Arg Gln Gln
                420                 425                 430
Gln Phe Arg Asp Gln Pro Lys Asp Gln Leu Cys Val Trp Val Tyr Gly
                435                 440                 445
Leu Phe Pro Asp Lys Pro Gly Asn Tyr Val Lys Pro Met Thr Glu
                450                 455                 460
Cys Thr Gly Glu Glu Ile Cys Glu Glu Trp Leu Tyr His Met Gly Val
465                 470                 475                 480
Pro Thr Asp Lys Ile Glu Ser Leu Ala Lys His His Ala Asn Thr Val
                485                 490                 495
Pro Val Met Met Pro Tyr Ile Thr Ala Phe Phe Met Pro Arg Ala Ala
                500                 505                 510
Gly Xaa Arg Pro Asp Val Val Pro Asp Gly Ala Val Asn Phe Ala Phe
                515                 520                 525
Leu Gly Gln Phe Ala Glu Thr Pro Arg Asp Thr Xaa Phe Thr Thr Glu
                530                 535                 540
Tyr Ser Met Arg Thr Gly Met Glu Ala Val Tyr Thr Leu Leu Gly Val
545                 550                 555                 560
Asp Arg Gly Val Pro Glu Val Trp Gly Ser Val Tyr Asp Val Arg Asn
                565                 570                 575
```

-continued

```
Leu Leu Asn Ala Thr Val Lys Leu Arg Asp Gly Ala Pro Val Thr Asp
            580                 585                 590

Met Lys Leu Asn Phe Ile Glu Xaa Ala Val Val Lys Lys Val Leu Lys
        595                 600                 605

Lys Leu Asp Gly Thr Asp Ile Ala Thr Leu Leu Arg Xaa Tyr His Val
    610                 615                 620
```

CONJUGATED LINOLEIC ACID ISOMERASE AND A PROCESS FOR THE PRODUCTION OF CONJUGATED LINOLEIC ACID

RELATED APPLICATIONS

This application claims the benefit of European Application Serial No. 01113962.3, filed Jun. 8, 2001, the entire contents of which are incorporated herein by this reference.

FIELD OF THE INVENTION

The present invention relates to a process for the production of conjugated linoleic acid and a process for the production of triglycerides with an increased content of conjugated linoleic acid.

Moreover, the invention relates to a nucleic acid sequence; a nucleic acid construct, a vector and transgenic organisms comprising at least one nucleic acid sequence or one nucleic acid construct which encodes a polypeptide with conjugated linoleic isomerase activity. Furthermore, the invention relates to the use of a microorganism of the genus *Bifidobacterium* as a probiotic.

BACKGROUND

Fatty acids and triglycerides have a multiplicity of applications in the food industry, animal nutrition, cosmetics and in the pharmaceutical sector. Depending on whether they are free saturated or unsaturated fatty acids or triglycerides with an increased content of saturated or unsaturated fatty acids, they are suitable for a very wide range of applications; thus, for example, polyunsaturated fatty acids are added to baby formula to increase the nutritional value. The various fatty acids and triglycerides are obtained mainly from microorganisms such as *Mortierella* or from oil-producing plants such as soya, oilseed rape, sunflowers and others, where they are usually obtained in the form of their triacyl glycerides. Alternatively, they are obtained advantageously from animals, such as fish. The free fatty acids are prepared advantageously by hydrolysis.

Whether oils with unsaturated or with saturated fatty acids are preferred depends on the intended purpose; thus, for example, lipids with unsaturated fatty acids, specifically polyunsaturated fatty acids, are preferred in human nutrition since they have a positive effect on the cholesterol level in the blood and thus on the possibility of heart disease. They are used in a variety of dietetic foodstuffs or medicaments.

Especially valuable and sought-after unsaturated fatty acids are the so-called conjugated unsaturated fatty acids, such as conjugated linoleic acid. A series of positive effects have been found for conjugated fatty acids; thus, the administration of conjugated linoleic acid reduces body fat in humans and animals, and increases the conversion of feed into body weight in the case of animals (WO 94/16690, WO 96/06605, WO 97/46230, WO 97/46118). By administering conjugated linoleic acid, it is also possible to positively affect, for example, allergies (WO 97/32008) or cancer (Banni et al., Carcinogenesis, Vol. 20, 1999: 1019–1024, Thompson et al., Cancer, Res., Vol. 57, 1997: 5067–5072).

Conjugated linoleic acid (=CLA) is an intermediate of linoleic acid metabolism in ruminants. CLA refers to a mixture of positional and geometric isomers of linoleic acid, involving double bonds at positions 9 and 11, 10 and 12 or 11 and 13, and has gained considerable attention in recent years because of the many beneficial effects attributed to the cis-9, trans-11 and trans-10, cis-12 isomers, in particular. These include anti-carcinogenic activity, antiatherogenic activity, the ability to reduce the catabolic effects of immune stimulation, the ability to enhance growth promotion and the ability to reduce body fat (Martin and Banni, 1998 for review, and references therein). The isomers can differ positionally (mainly at positions 7 and 9, 9 and 11; or 10 and 12) (Ha et al., 1987) and geometrically (cis-cis, cis-trans, trans-cis, trans-trans). Of the individual isomers of CLA, cis-9, trans-11-octadecadienoic acid has been implicated as the most biologically active because it is the predominant isomer incorporated into the phospholipids of cell membranes, liver phospholipids and triglycerides (Kramer et al., 1998). This is the only isomer incorporated into the phospholipid fraction of cell membranes of animals fed a mixture of CLA isomers (Ha et al., 1990; Ip et al., 1991). This isomer is also the predominant dietary form of CLA, obtained from fats derived from ruminant animals, including milk, dairy products and meat (Chin et al., 1992, O'Shea et al., 2000).

Studies have shown that CLA may have potential in the prevention of a wide range of human medical conditions, and a number of potential health benefits have been described for CLA, including as mentioned above anticarcinogenic activity, antiatherogenic activity, potential in the prevention of diabetes, obesity and bone disorders. Given that dietary CLA has the potential to beneficially affect human health, it is important to identify effective strategies to enrich the natural form of CLA in food products. Currently, the effective level of dietary CLA for disease prevention in humans is not known. Furthermore, the long-term health implications of a low dietary CLA intake at critical stages throughout life are unknown, as for example in formula-fed infants, compared with breast-fed infants, the latter group receiving a relatively higher CLA intake. In the rodent model, dietary CLA was more effective as an anti-carcinogen when consumed during periods of active mammary gland development (Ip et al., Nutr. Cancer, 1995, 24: 241–247), which may indicate that increased CLA intake during adolescence might preferentially decrease the risk of cancer in women.

Few data concerning the CLA intake are available. In Germany the daily CLA intake has been estimated to be 0.36 g/day for women and 0.44 g/day for men (Fritsche et al., 1998). CLA in human tissue is predominantly the isomere cis-9, trans-11-octa-decadienoic acid (>95%), three minor isomers have also been identified. Trans-9, trans-11–18:2, cis-9, cis-11–18:2 and trans9, cis-11–18:2, [Fritsche et al., Zeitschrift Lebensmittel. Untersuchung Forschung A-Food Research & Technology 205:415–418 (1997)]. The origin is thought to be dietary and the consumption of cheddar cheese, a good source of CLA, has been shown to enhance plasma CLA levels in men, [Huang et al. *Nutr. Res.* 14:373–386 (1994)]. In another study it was found that the relationship between milk fat intake and the occurence of cis-9, trans-11-octadecadienoic acid in human tissue was significantly correlated, [Jiang et al., *Am. J. Clin. Nutr.* 70:21–29 (1999)]. Safflower oil, a rich source of linoleic acid, did not increase plasma CLA levels suggesting that the intestinal flora of humans do not possess the ability to convert linoleic acid to conjugated linoleic acid, however a CLA increase was observed in some subjects [Herbel et al., Am. J. Clin. Nutr. 67: 332–337 (1998)]. Dietary trans fatty acid has been shown to increase serum CLA, [Salminen et al., Nutritional Biochemistry 9: 93–98 (1998)]. It was in this study concluded that CLA may be formed by desaturation of trans fatty acid possibly by a liver enzyme as has been described for rats.

The principial dietary sources of CLA are milk, dairy products and meat from ruminants, but as a result of differences in environmental conditions and diet of the ruminant species, the CLA content of milk and beef fat vary substantially [Michelle et al., Advances in Conjugated Linoleic Acid Research, Volume 1 (1999)]. Among the richest dietary sources of CLA are milk, dairy products, beef and lamb (Chin et al., J. Food Comp. and Anal., 1992, 5: 185–197; Fritsche and Steinhart, Z. Lebensm. Unters. Forsch., 1998, A206: 77–82 and Lipid, 1998, 6S: 190–210).

In fat from ruminant meats and dairy products, the cis-9, trans-11 CLA isomer is present at 80–90% of the total CLA isomers (Chin et al., J. Food Comp. and Anal., 1992, 5: 185–197).

As mentioned above the origin of CLA in foods is mainly due to the biohydrogenation of dietary linoleic acid by anaerobic rumen bacteria. Accordingly the main dietary sources of CLA are meat from ruminant animals and dairy products, and the main CLA isomer found is cis-9, trans-11-C18:2, (80–90%). In uncooked meats, lamb and beef answer for the highest CLA levels 5.6 mg/g of fat in lamb and 4.3 mg/g of fat in beef (Chin et al., 1992; Fritsche and Steinhart, 1998 ). CLA levels in milk varies with season, highest values occuring when pastures are lush and rich in PUFAs, hence levels of CLA in dairy products such as cheese also varies. In vegetable oils CLA is present in low amounts (0.2–0.7 mg/g fat) and contain higher levels of the isomer trans-10, cis-12-C18:2 (~40%) (Chin et al., 1992). Since fatty acids with conjugated double bonds are a well-known phenomena in plants, specific enzyme systems are belived to be involved. Meats from non-ruminant animals can contain CLA in lower amounts and it may occur from dietary sources such as feeding meat meal. It could also be explained by formation of CLA by intestinal flora as has been shown for rats (Chin et al., J. Nutr., 1993, 124: 694–701). CLA can also be produced by free radical-based double bond shifting during autooxidation and during partial hydrogenation performed industrially.

CLA can be manufactured synthetically from alkaline isomerization of linoleic and linolenic acids, or vegetable oils containing linoleic or linolenic acids. Two reactions are catalyzed when heating oil at 180° C. under alkaline conditions; hydrolysis of the fatty acid ester bond from the triglyceride lipid backbone, which produces free fatty acids, and conjugation of unconjugated unsaturated fatty acids with two or more approproiate double bonds (WO 99/32604). This method produces about 20–35% cis-9, trans-11 CLA and about the same amount of trans-10, cis-12 CLA, but enrichment of either of the isomers relative to the other is possible by using a fractional crystallization procedure.

In addition other isomers are produced mainly trans, trans isomers.

The chemical preparation of conjugated fatty acids, for example conjugated linoleic acid, is also described in U.S. Pat. Nos. 3,356,699 and 4,164,505.

The presence of conjugated unsaturated fatty acids in milk fat was first established by Booth et al. *Bioch. J.* 29, 133–137 (1935), who also showed that these fatty acids increased in milk fat when cows were turned out to pasture after winter, by demonstrating an increased absorption of the fatty acids in the ultra-violet (UV) region at 230 nm. CLA is formed in the rumen during microbial biohydrogenation of dietary linoleic acid (Kepler and Tove, 1969 Methods in enzymology Vol XIV, p105; J. Biol. Chem., Vol 246, No. 14, 1970: 3612–3620 and J. Biol. Chem., Vol 246, No. 9, 2765–2771). The complete biohydrogenation of linoleic acid in the rumen is a three step process, yielding C 18:0, stearic acid, as an end product. The first reaction, the conversion of linoleic acid to cis-9, trans-11 CLA by linoleic acid isomerase of rumen bacteria occurs very rapidly, followed by slower conversion to trans-11-C 18:1 (FIG. 1). Some of the CLA formed in the rumen is absorbed into blood and incorporated into milk fat. In addition to the biohydrogenation reaction leading to CLA synthesis, CLA can also be produced endogenously from trans-11-C 18:1 in mammary tissues. Trans-11-C 18:1 accumulates in the rumen due to the slower conversion step to stearic acid, and following absorption from the digestive tract is utilized by different tissues e.g. the mammary gland as a substrate for CLA synthesis by the action of $\Delta$-9-desaturase. Indeed, this may be the major pathway of CLA synthesis in lactating cows, accounting for about 64% of the CLA in milk fat.

In addition member of strains of propionibacteria were previously identified to synthesise CLA from linoleic acid by Jiang et al. (1998).

WO 99/29886 describes the use of certain bacterial strains found among food grade bacteria, particularly among dairy starter cultures, which have the ability to produce CLA in vitro by fermentation. Furthermore WO 99/29886 decribes that said bacteria may be used to provide food or feed products enriched in CLA, and also pharmaceutical products containing CLA as active ingredients.

Isomerases are enzymes which bring about an isomerisation of substrate. Linoleic acid isomerase catalyzes the isomerisation reaction of lionoleic acid to cis-9, trans-11-octadecadienoic acid. This membrane bound enzyme was isolated and characterised by Kepler & Tove (1969). The isomerisation reaction occurs in the middle of a long hydrocarbon chain remote from any functional group and requires no cofactors. The enzyme exhibits max activity with substrates linoleic and linolenic acid within a narrow concentration range. Three parameters are involved in the binding of substrate to linoleic acid isomerase: 1.) the $\pi$ system of a substrate double bond, 2.) hydrophobic interaction and 3.) hydrogen bonding of the substrate carboxyl group. A proposed model for the isomerization of linoleic acid by linoleic acid isomerase is illustrated in FIG. 2. Pictured at the active site are an electrophile (E) that interacts with one of the substrate double bonds, and two basic centers, one of wich (B) is hydrogen bonded to the carboxyl group and the other (B—H) which serves as a donor for the hydrogen added at C-13 (FIG. 2).

WO 99/32604 describes a linoleate isomerase from *Lactobacillus reuteri*. The enzyme activity leads to the conversion of linoleic acid to six different CLA species which are as follows: (cis,trans)-9,11-CLA, (trans,cis)-10,12-CLA, (cis,cis)-9,11-CLA, (cis,cis)-10,12-CLA, (trans,trans)-9,11-CLA and (trans,trans)-10,12-CLA.

The disadvantages of the abovementioned process is that the yield of the reaction is very low, the purity of the CLA produced is for an industrial process not sufficient and that the process takes place with only low space-time yields. This leads to economically unattractive processes.

Thus, there is still a great need for a single, economic birthdenological industrial process for the production of CLA which does not have the abovementioned disadvantages and therefore for new genes which encode enzymes which participate in the biosynthesis of conjugated linoleic acid and which allow to synthesize and produce it on an industrial scale.

BRIEF DESCRIPTION OF DRAWINGS

FIG. 1 depicts the biohydrogenation of linoleic acid in the rumen.

FIG. 2 depicts the proposed model for the isomerization of linoleic acid by linoleic acid isomerase.

FIG. 3 depicts the method for chromosomal walking by inverse PCR.

FIG. 4 depicts a map of the pCR®2.1-TOPO® vector.

FIG. 5 graphically depicts the fatty acid composition of supernatant following incubation in MRS medium containing 0.5 mg/ml linoleic acid with *B. breve* 2258 for 24 hours as compared to the control of *B. breve* 2258 incubated in MRS medium alone.

FIG. 6 depicts a GLC chromatogram of *B. breve* 2258, with a control supernatant.

FIG. 7 depicts a GLC chromatogram of *B. breve* 2258, with a linoleic acid supernatant.

FIG. 8 depicts a chromatogram of conjugated linoleic acid standard (Nu- Chek- Prep. Inc, Elysian, Minn.). Separation was performed on Chrompack CP Sil 88 Column (Chrompack, Middleburg, The Netherlands) (60 m×0.25 mm i.d., 0.20 m film thickness). The retention time on this column is different from the column used for the bacterial fatty acids.

FIG. 9 graphically depicts the fatty acid composition of pellets following incubation in MRS medium containing 0.5 mg/ml linoleic acid with *B. breve* for 24 hours. The control was *B. breve* 2258 icubated in MRS medium alone.

FIG. 10 graphically depicts the fatty acid composition of supernatant following incubation in MRS medium containing 0.5 mg/ml cis-9, trans-11 CLA with *B. breve* 2258 for 48 hours. The control was *B. breve* 2258 incubated in MRS medium alone.

FIG. 11 depicts a GLC chromatogram of *B. breve* 2258 with conjugated linoleic acid as supernatant.

FIG. 12 graphically depicts the fatty acid composition of pellets following incubation in MRS medium containing 0.5 mg/ml cis-9, trans-11 conjugated linoleic acid with *B. breve* 2258 for 48 hours. The control was *B. breve* 2258 incubated in MRS medium alone.

DESCRIPTION OF THE INVENTION

It is an object of the present invention to provide other isomerases for the synthesis of unsaturated conjugated fatty acids.

We have found that this object is achieved by an isolated nucleic acid sequence which encodes a polypeptide with conjugated linoleic acid isomerase activity, selected from the following group:
a) a nucleic acid sequence with the sequence shown in SEQ ID NO: 1,
b) nucleic acid sequences which, as a result of the degeneracy of the genetic code, are derived from the nucleic acid sequence shown in SEQ ID NO: 1,
c) derivatives of the nucleic acid sequence shown in SEQ ID NO: 1 which encode polypeptides with the amino acid sequences shown in SEQ ID NO: 2 and which have at least 75% identity at amino acid level without substantially reducing the enzymatic activity of the polypeptides.

These conjugated linoleic acid isomerases can be found in organisms, advantageously microorganisms such as bacteria. The enzyme or the enzymes have a high enzymatic activity for the hydrolytic conversion of linoleic acid into conjugated linoleic acid.

A derivative (or derivatives) is/are to be understood as meaning, for example, functional homologs of the enzyme encoded by SEQ ID NO: 1 or its enzymatic activity, viz. enzymes which catalyze the same enzymatic reactions as the enzyme encoded by SEQ ID NO:1. These genes also allow an advantageous preparation of unsaturated conjugated fatty acids preferably conjugated linoleic acid. Unsaturated fatty acids are to be understood, in the following text, as meaning polyunsaturated fatty acids whose double bonds may be conjugated or not conjugated. The sequence given in SEQ ID NO:1 encodes a novel, unknown isomerase which participates in the synthesis of conjugated linoleic acid in the genus *Bifidobacterium* especially *Bifidobacterium breve*. The enzyme converts (9Z,12Z)octadecadienoic/linoleic acid to (cis-9,trans-11) octadecaconjudienoic/conjugate linoleic acid. This is termed conjugated linoleic acid isomerase or in short terms isomerase hereinbelow.

The nucleic acid sequences according to the invention can in principle be identified and isolated from all organisms. SEQ ID NO: 1 or its homologs can advantageously be isolated from fungi, yeasts or bacteria. Bacteria which may be mentioned are Gram-negative and Gram-positive bacteria. The nucleic acid(s) [the plural and singular are intended to have the same meaning for the application] according to the invention are preferably isolated by methods known to the skilled worker from Gram-positive bacteria such as *Propionibacterium, Lactococcus, Bifidobacterium* or *Lactobacillus*, advantageously from *Bifidobacterium*.

The nucleic acid sequence according to the invention or its fragments can be used advantageously for isolating further genomic sequences by means of homology screening.

The abovementioned derivatives can be isolated, for example, from other microorganisms such as rumen or intestine bacteria such as *Butyrivibrio, Propionibacterium* or bacteria which can be isolated for example from dairy products such as *Lactococcus* or *Lactobacillus*.

Such microorganism and the ability of certain rumen-derived strains, including *Butyrivibrio fibrisolvens* to form CLA from dietary linoleic acid are decribed by Kepler and Tove [The Journal of Biological Chemistry, Vol.246 No 14: 3612–3620 (1970)], it has also been shown that certain cultures used in food fermentations possess the ability to generate cis-9, trans-11 CLA. Strains of the intestinal flora in rats (Chin et al., J. Nutr. 124, 1993: 694–701), two strains of *Propionibacterium freudenreichii* spp. *freudenreichii* and one strain of *P. freudenreichii* subsp. *shermanii* (Jiang et al., J. Appl. Microbiol., 85, 1998: 95–102), and six lactic cultures, including *L. acidophilus* (Lin et al., 1999) have been shown to possess this capability. In this study, we assessed a collection of strains, many which are human intestinal isolates (previously isolated from the human GIT) with probiotic potential, for ability to form the cis-9, trans-11 CLA isomer, using linoleic acid as the substrate.

Derivatives or functional derivatives of the sequence given in SEQ ID No.1 are furthermore to be understood as meaning, for example, allelic variants which have at least 75% homology (=identity) at the derived amino acid level, preferably at least 80% homology, especially preferably at least 85% homology, very especially preferably 90% homology, most preferably 95%, 96%, 97%, 98% or 99% homology. The homology (=identity) was calculated over the entire amino acid range. The program used was PileUp (J. Mol. Evolution., 25 (1987), 351–360, Higgins et al., CABIOS, 5 1989: 151–153). The amino acid sequence derived from the abovementioned nucleic acid can be seen from the sequence SEQ ID NO: 2. Allelic variants encompass, in particular, functional variants which can be obtained from the sequence shown in SEQ ID NO: 1 by means of deletion, insertion or substitution of nucleotides, the enzymatic activity of the derived synthetic proteins being retained.

Such DNA sequences can be isolated from other microorganism as mentioned above, starting from the DNA sequence described in SEQ ID NO: 1 or parts of these sequences, for example using customary hybridization methods or the PCR technique. These DNA sequences hybridize with the sequences mentioned under standard conditions. It is advantageous to use, for the hybridization, short oligonucleotides, for example from the conserved regions, which can be determined by the skilled worker by comparison with other known isomerase genes.

Alternatively, it is possible to use longer fragments of the nucleic acids according to the invention or the full sequences for the hybridization. Depending on which nucleic acid: oligonucleotide, longer fragment or full sequence, or depending on which nucleic acid type, viz. DNA or RNA, is used for the hybridization, these standard conditions vary. Thus, for example, the melt temperatures for DNA:DNA hybrids are approximately 10° C. lower than those of equally long DNA:RNA hybrids.

Depending on the nucleic acid, standard conditions are understood as meaning, for example, temperatures between 42 and 58° C. in an aqueous buffer solution with a concentration of between 0.1 and 5×SSC (1×SSC=0.15 M NaCl, 15 mM sodium citrate, pH 7.2) or additionally in the presence of 50% formamide such as, for example, 42° C. in 5×SSC, 50% formamide. The hybridization conditions for DNA:DNA hybrids are advantageously 0.1×SSC and temperatures between approximately 20° C. and 45° C., preferably between approximately 30° C. and 45° C. The hybridization conditions for DNA:RNA hybrids are advantageously 0.1× SSC and temperatures between approximately 30° C. and 55° C., preferably between approximately 45° C. and 55° C. These temperatures which are indicated for the hybridization are examples of calculated melting point data for a nucleic acid with a length of approx. 100 nucleotides and a G+C content of 50% in the absence of formamide. The experimental conditions for the DNA hybridization are described in relevant genetics textbooks such as, for example, by Sambrook et al., "Molecular Cloning", Cold Spring Harbor Laboratory, 1989 and can be calculated using formulae known to the skilled worker, for example as a function of the length of the nucleic acids, the type of hybrid or the G+C content. The skilled worker can find further information on hybridization in the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

Derivatives are furthermore to be understood as meaning homologs of the sequence SEQ ID NO: 1, for example insect homologs, truncated sequences, simplex DNA of the coding and noncoding DNA sequence or RNA of the coding and noncoding DNA sequence.

Homologs of the sequence SEQ ID NO: 1 are also to be understood as meaning derivatives such as, for example, promoter variants. These variants can be altered by one or more nucleotide exchanges, by insertion(s) and/or deletion(s), without, however, adversely affecting the functionality or efficacy of the promoters. Moreover, it is possible to increase the efficacy of the promoters by altering their sequence or to exchange them completely by more efficient promoters from other organisms, including other species.

Derivatives are also advantageously to be understood as meaning variants whose nucleotide sequence in the region −1 to −2000 upstream of the start codon was altered in such a way that gene expression and/or protein expression is altered, preferably increased. Moreover, derivatives are also to be understood as meaning variants whose 3' end was altered.

To achieve optimal expression of heterologous genes in organisms, it is advantageous to alter the nucleic acid sequences in accordance with the specific codon usage used in the organism. The codon usage can be determined readily by using computer evaluations of other, known genes of the organism in question.

The amino acid sequences according to the invention are to be understood as meanings which contain an amino acid sequence shown in SEQ ID NO: 2 or a sequence obtainable therefrom by the substitution, inversion, insertion or deletion of one or more amino acid residues, the enzymatic activity of the protein shown in SEQ ID NO: 2 being retained or not reduced substantially. The term not reduced substantially is to be understood as meaning all enzymes which still have at least 10%, preferably 20%, especially preferably 30% of the enzymatic activity of the starting enzyme. For example, certain amino acids may be replaced by others with similar physico-chemical properties (spatial dimension, basicity, hydrophobicity and the like). For example, arginine residues are exchanged for lysine residues, valine residues for isoleucine residues or aspartic acid residues for glutamic acid residues. Alternatively, it is possible to exchange the sequence of, add or remove one or more amino acids, or two or more of these measures may be combined with each other.

The nucleic acid construct or nucleic acid fragment according to the invention is to be understood as meaning the sequence given in SEQ ID NO: 1, sequences which are the result of the genetic code and/or their functional or nonfunctional derivatives, all of which have been linked functionally to one or more regulatory signals, advantageously for increasing gene expression. These regulatory sequences are, for example, sequences to which inductors or repressors bind and thus regulate the expression of the nucleic acid. In addition to these novel regulatory sequences, or instead of these sequences, the natural regulation of these sequences upstream of the actual structural genes may still be present and, if desired, may have been genetically altered in such a way that the natural regulation has been switched off and the expression of the genes increased. However, the expression of the gene construct may also have a simpler structure, viz. no additional regulatory signals have been inserted upstream of the sequence or its derivatives and the natural promoter with its regulation has not been removed. Instead, the natural regulatory sequence has been mutated in such a way that regulation no longer takes place and gene expression is increased. These altered promoters may also be placed upstream of the natural gene on their own, in order to increase activity. In addition, the gene construct can also advantageously contain one or more so-called enhancer sequences functionally linked to the promoter, and these allow an increased expression of the nucleic acid sequence. It is also possible to insert, at the 3' end of the DNA sequences, additional advantageous sequences such as further regulatory elements or terminators. One or more copies of the conjugated linoleic acid isomerase gene may be contained in the gene construct.

Advantageous regulatory sequences for the process according to the invention are contained, for example, in promoters such as cos, tac, trp, tet, trp-tet, lpp, lac, lpp-lac, lacI$^q$, T7, T5, T3, gal, trc, ara, SP6, λ-$P_R$ or in the λ-$P_L$ promoter, all of which are advantageously used in Gram-negative bacteria. Other advantageous regulatory sequences are contained, for example, in the Gram-positive promoters amy and SPO2, in the yeast or fungal promoters ADC1, MFα, AC, P-60, CYC1, GAPDH, TEF, rp28, ADH.

In principle, all natural promoters with their regulatory sequences as those mentioned above may be used for the process according to the invention. In addition, synthetic promoters may also advantageously be used.

The nucleic acid construct advantageously contains, for expression of the genes present, in addition 3' and/or 5' terminal regulatory sequences to increase expression, these being selected for optimal expression depending on the selected host organism and gene or genes.

These regulatory sequences are intended to make specific expression of the genes and protein expression possible. This may mean, for example depending on the host organism, that the gene is expressed or overexpressed only after induction, or that it is expressed and/or overexpressed immediately.

The regulatory sequences or factors may for this purpose preferably have a beneficial effect on expression of the introduced genes, and thus increase it. Thus, an enhancement of the regulatory elements can advantageously take place at the level of transcription, by using strong transcription signals such as promoters and/or enhancers. However, it is also possible to enhance translation by, for example, improving the stability of the mRNA.

The nucleic acid construct (=gene construct, nucleic acid construct, nucleic acid fragment) may also contain further genes to be introduced into organisms. These genes can be under separate regulation or under the same regulatory region as the isomerase gene according to the invention. These genes are, for example, other biosynthesis genes, advantageously of the fatty acid and lipid biosynthesis, which allow increased synthesis of the isomerase starting material such as linoleic acid.

For optimal expression of heterologous genes in organisms it is advantageous to modify the nucleic acid sequences in accordance with the specific codon usage of the organism. The codon usage can easily be established on the basis of computer analyses of other, known genes of the relevant organism.

For expression in a host organism, for example a microorganism such as fungi or bacteria, the nucleic acid fragment is advantageously inserted into a vector such as, for example, a plasmid, a phage or other DNA, which vector allows optimal expression of the genes in the host. Examples of suitable plasmids are, in *E. coli*, pLG338, pACYC184, pBR322, pUC18, pUC19, pKC30, pRep4, pHS1, pHS2, pPLc236, pMBL24, pLG200, pUR290, pIN-III[113]-B1, λgt11 or pBdCI, in *Streptomyces* pIJ101, pIJ364, pIJ702.or pIJ361, in *Bacillus* pUB110, pC194 or pBD214, in *Corynebacterium* pSA77 or pAJ667, in fungi pALS1, pIL2 or pBB116, in yeasts 2 μM, pAG-1, YEp6, YEp13 or pEM-BLYe23, or derivatives of the abovementioned plasmids. The plasmids mentioned represent a small selection of the plasmids which are possible. Other plasmids are well known to the skilled worker and can be found, for example, in the book Cloning Vectors (Eds. Pouwels P. H. et al. Elsevier, Amsterdam-New York-Oxford, 1985, ISBN 0 444 904018). Suitable plant vectors are described, inter alia, in "Methods in Plant Molecular Biology and Biotechnology" (CRC Press), Chapter 6/7, pp. 71–119.

In principle all organism are useful as host for the inventive process such as fungi, bacteria, yeasts, animals or plants.

In addition to plasmids, vectors are also to be understood as meaning all the other vectors which are known to the skilled worker, such as, for example, phages, viruses such as SV40, CMV, baculovirus, adenovirus, transposons, IS elements, phasmids, phagemids, cosmids, linear or circular DNA. These vectors can be replicated autonomously in the host organism or replicated chromosomally. Autonomous replication is preferred.

The vector advantageously contains at least one copy of the nucleic acid sequence according to the invention and/or of the nucleic acid fragment according to the invention.

To increase the gene copy number, the nucleic acid sequences or homologous genes can be introduced, for example, into a nucleic acid fragment or into a vector which preferably contains the regulatory gene sequences assigned to the genes in question, or analogously acting promoter activity. Regulatory sequences which are used in particular are those which increase gene expression.

To express the other genes contained, the nucleic acid fragment advantageously additionally contains 3'- and/or 5'-terminal regulatory sequences to increase expression, these sequences being selected for optimal expression, depending on the host organism chosen and the gene or genes.

These regulatory sequences should allow the targeted expression of the genes and protein expression. Depending on the host organism, this may mean, for example, that the gene is expressed and/or overexpressed only after induction, or that it is expressed and/or overexpressed immediately.

The regulatory sequences or factors can preferably have a positive effect on, and thus increase, the gene expression of the genes introduced. Thus, strengthening of the regulatory elements can advantageously take place at the transcriptional level by using strong transcription signals such as promoters and/or enhancers. In, addition, however, strengthening of translation is also possible, for example by improving mRNA stability.

In a further embodiment of the vector, the gene construct according to the invention can advantageously also be introduced into the organisms in the form of a linear DNA and integrated into the genome of the host organism by means of heterologous or homologous recombination. This linear DNA may consist of a linearized plasmid or only of the nucleic acid fragment as vector or of the nucleic acid sequence according to the invention.

The nucleic acid sequence according to the invention is advantageously cloned into a nucleic acid construct together with at least one reporter gene, and the nucleic acid construct is introduced into the genome. This reporter gene should allow easy detectability via a growth assay, a fluorescence assay, a chemo assay, a bioluminescence assay or a resistance assay, or via a photometric measurement. Examples of reporter genes which may be mentioned are genes for resistance to antibiotics or herbicides, hydrolase genes, fluorescence protein genes, bioluminescence genes, sugar metabolism genes or nucleotide metabolism genes, or biosynthesis genes such as the Ura3 gene, the Ilv2 gene, the luciferase gene, the β-galactosidase gene, the gfp gene, the 2-deoxyglucose-6-phosphate phosphatase gene, the β-glucuronidase gene, the β-lactamase gene, the neomycin phosphotransferase gene, the hygromycin phosphotransferase gene or the BASTA (=gluphosinate) resistance gene. These genes allow the transcriptional activity, and thus gene expression, to be measured and quantified easily. In this way, genome sites which show different productivity can be identified.

In a further advantageous embodiment, the nucleic acid sequence according to the invention may also be introduced into an organism on its own.

If it is intended to introduce, into the organism, other genes in addition to the nucleic acid sequence according to the invention, all can be introduced into the organism in a single vector with a reporter gene, or each individual gene with a reporter gene per vector, it being possible for the various vectors to be introduced simultaneously or in succession.

The host organism (=transgenic organism) advantageously contains at least one copy of the nucleic acid according to the invention and/or of the nucleic acid construct according to the invention.

In principle, the nucleic acid according to the invention, the nucleic acid construct or the vector can be introduced into organisms, for example plants, by all methods known to the skilled worker.

In the case of microorganisms, the skilled worker can find suitable methods in the textbooks by Sambrook, J. et al. (1989) Molecular cloning: A laboratory manual, Cold Spring Harbor Laboratory Press, by F. M. Ausubel et al. (1994) Current protocols in molecular biology, John Wiley and Sons, by D. M. Glover et al., DNA Cloning Vol.1, (1995), IRL Press (ISBN 019-963476-9), by Kaiser et al. (1994) Methods in Yeast Genetics, Cold Spring Harbor Laboratory Press or by Guthrie et al. Guide to Yeast Genetics and Molecular Biology, Methods in Enzymology, 1994, Academic Press.

Suitable organisms or host organisms (transgenic organism) for the nucleic acid according to the invention, the nucleic acid construct or the vector are, in principle, all organisms which are capable of synthesizing unsaturated fatty acids, and which are suitable for the expression of recombinant genes. Examples which may be mentioned are transgenic plants, transgenic microorganisms such as fungi, for example the genus *Mortierella, Saprolegnia* or *Pythium*, transgenic bacteria such as the genus *Escherichia, Bifidobacterium, Brevibacterium* or *Corynebacterium* or yeasts such as the genus *Saccharomyces*. Preferred organisms are those which are naturally capable of synthesizing oils in substantial amounts, like fungi such as *Mortierella alpina, Pythium insidiosum* or plants such as soya, oilseed rape, flax, coconut palms, oil palms, safflower or sunflowers, or yeasts such as *Saccharomyces cerevisiae*, with soya, oilseed rape, flax, sunflowers, fungi such as *Mortierella* or bactria such as the genus *Bifidobacterium, Brevibacterium* or *Corynebacterium* being especially preferred. In principle, transgenic animals, for example *Caenorhabditis elegans*, are also suitable as host organisms.

Advantageously the least organism should grow in the precense of more than 0.5 mg/ml linoleic acid, preferably more than 1 mg/ml, more preferably more than 1.5 mg/ml and most preferably more than 2 mg/ml linoleic acid. The skilled worker knows how to identify such prefered organism by using a simple gows assay.

With regard to the nucleic acid sequence as depicted in SEQ ID NO: 1, a nucleic acid construct which contains said nucleic acid sequence or an organism (=transgenic organism) which is transformed with said nucleic acid sequence or said nucleic acid construct, "transgene" means all those constructs which have been brought about by genetic manipulation methods and in which either a) the nucleic acid sequence as depicted in SEQ ID NO: 1 or a derivative thereof, or b) a genetic regulatory element, for example a promoter, which is functionally linked to the nucleic acid sequence as depicted in SEQ ID NO: 1 or a derivative thereof, or c) (a) and (b) is/are not present in its/their natural genetic environment or has/have been modified by means of genetic manipulation methods, it being possible for the modification to be, by way of example, a substitution, addition, deletion, inversion or insertion of one or more nucleotide radicals. "Natural genetic environment" means the natural chromosomal locus in the organism of origin or the presence in a genomic library. In the case of a genomic library, the natural, genetic environment of the nucleic acid sequence is preferably at least partially still preserved. The environment flanks the nucleic acid sequence at least on one side and has a sequence length of at least 50 bp, preferably at least 500 bp, particularly preferably at least 1000 bp, very particularly preferably at least 5000 bp.

The use of the nucleic acid sequence according to the invention or of the nucleic acid construct according to the invention for the generation of transgenic plants is therefore also subject matter of the invention.

In the conversion with the enzyme according to the invention, one double bond is shifted so that the double bonds which participate in the reaction are conjugated (FIG. 2).

The enzyme (=conjugated linoleic isomerase) advantageously catalyzes the conversion of linoleic acid (18:2, 9Z,12Z) to conjugated cis-9, trans-11 linoleic acid.

The invention furthermore relates to a process for the production of conjugated unsaturated fatty acids especially conjugated linoleic acid, which comprises introducing at least one above-described nucleic acid sequence according to the invention or at least one nucleic acid construct according to the invention into a preferentially oil-producing organism, growing this organism, isolating the oil contained in the organism and liberating the fatty acids contained in the oil.

The invention also includes a process for the production of triglycerides with an increased content of conjugated unsaturated fatty acids especially conjugated linoleic acid, which comprises introducing at least one above-described nucleic acid sequence according to the invention or at least one nucleic acid construct according to the invention into a preferentially oil-producing organism, growing this organism and isolating the oil contained in the organism.

Both processes advantageously allow the synthesis of fatty acids of triglycerides with an increased content of unsaturated fatty acids such as conjugated linoleic acid.

The host organisms advantageously contain 0.5 U/g DBM (=dry bio-mass) CLA isomerase activity, preferably 4 U/g DBM, particularly preferably 20–150 U/g DBM, very particularly preferably 40–150 U/g DBM.

The process according to the invention is advantageously carried out at a temperature between 0° C. and 95° C., preferably between 10° C. and 85° C., particularly preferably between 15° C. and 75° C., most preferably between 20° C. and 60° C.

The pH in the process (in vitro) according to the invention is advantageously kept between pH 4 and 12, preferably between pH 6 and 9, particularly preferably between pH 6 and 8, very particularly preferably between pH 6.0 and 7.5.

The purities of the different CLA isomers which are produced in the inventive process is of at least 70%, preferably of at least 80%, particularly preferably of at least 90%, very particularly preferably at least 98%.

It is possible to use for the process according to the invention growing cells which comprise the nucleic acids, nucleic acid constructs or vectors according to the invention. It is also possible to use resting or disrupted cells. Disrupted cells mean, for example, cells which have been made permeable by treatment with, for example, solvents, or cells which have been ruptured by an enzyme treatment, by a mechanical treatment (for example French press or ultrasound) or by another method. The crude extracts obtained in this way are advantageously suitable for the process according to the invention. Purified or partially purified enzymes can also be used for the process. Likewise suitable are immobilized microorganisms or enzymes which can advantageously be used in the reaction.

If free organisms or enzymes are used for the process according to the invention, these are expediently removed, for example by filtration or centrifugation, before the extraction. It is advantageous that this is unnecessary on use of immobilized organisms or enzymes, but it may still take place.

With the types of work up mentioned, the product of the process (=conjugated unsaturated fatty acids, especially CLA preferably. 9-cis, 11-trans CLA) according to the invention can be isolated in yields of from 20 to 100%, preferably from 30 to 100%, particularly preferably from 50 to 100%, more particularly preferably from 60 to 100%, 70 to 100%, 80 to 100%, 90 to 100%, based on the amount of linoleic acid employed for the reaction. In addition, the products have a high isomeric purity, which can advantageously be further increased where necessary by the crystallization. The inventive process leads to cis-9, trans-11 octadecadienoic acid as major product.

Linoleic acid as a major starting material can be added to the reaction mixture batchwise, semibatchwise or continuously.

The process according to the invention can be carried out in vivo or in vitro batchwise, semibatchwise or continuously.

The concentration of the starting material for the process which is preferably linoleic acid is higher than 0,5 mg/ml, preferably higher than 2 mg/ml, more preferably higher than 3 mg/ml.

The concentration of CLA as product of the inventive process in the culture medium is higher than 1 mg/ml, preferably higher than 2 mg/ml, more preferably higher than 3 mg/ml.

The products obtained in this way are suitable as starting material for the synthesis of mono-, di- or triglycerols and derivatives thereof. These substances and the isomer pure CLA obtained can be used in combination with one another or alone for producing drugs, foodstuffs, animal feeds or cosmetics.

Examples of organisms for the abovementioned processes are plants such as *Arabidopsis*, soya, peanuts, castor, sunflowers, corn, cotton, flax, oilseed rape, coconut palms, oil palms, safflower (*Carthamus tinctorius*) or cacao, microorganisms such as the fungi *Mortierella*, *Saprolegnia* or *Pythium*, bacteria such as gram-positive or gram-negative bacteria of the *genera Escherichia, Lactobacillus, Lactococcus, Propionibacterium, Bifidobacterium, Brevibacterium, Corynebacterium, Pediococcus* or *Butyrivibrio*, yeasts such as the *genus Saccharomyces*. Preferred organisms are those which can naturally synthesize oils in substantial amounts, such as fungi, for example *Mortierella alpina*, *Pythium insidiosum*, or plants such as soya, oilseed rape, flax, coconut palms, oil palms, safflower, castor, peanuts, cacao or sunflowers, or yeasts such as *Saccharomyces cerevisiae* or bacteria such as *Propionibacterium freudenreichii, Propionibacterium acidipropionici, Propionibacterium acnes, Propionibacterium avidum, Propionibacterium granulosum, Propionibacterium jensenii, Propionibacterium lymphophilum, Propionibacterium propionicum, Propionibacterium theonii, Pediococcus acidilactici, Pediococcus damnosus, Pediococcus dextrinicus, Pediococcus halophilus, Pediococcus parvulus, Pediococcus pentosaceus, Bifidobacterium breve, Bifidobacterium dentium, Bifidobacterium adolescentis, Bifidobacterium longum, Bifidobacterium angulatum, Bifidobacterium bifidum, Bifidobacterium lactis, Bifidobacterium asteroides, Bifidobacterium boum, Bifidobacterium catenulatum, Bifidobacterium choerinum, Bifidobacterium coryneforme, Bifidobacterium cuniculi, Bifidobacterium gallinarum, Bifidobacterium globosum, Bifidobacterium indicum, Bifidobacterium infantis, Bifidobacterium magnum, Bifidobacterium merycicum, Bifidobacterium minimum, Bifidobacterium pseudocatenulatum, Bifidobacterium pseudolongum, Bifidobacterium pullorum, Bifidobacterium subtile, Bifidobacterium suis, Bifidobacterium thermophilum, Butyrivibrio fibrisolvens, Butyrivibrio crossotus, Lactobacillus acidophilus, Lactobacillus acetotolerans, Lactobacillus agilis, Lactobacillus alimentarius, Lactobacillus amylovorus, Lactobacillus animalis, Lactobacillus aviarius, Lactobacillus bifermentans, Lactobacillus bifidus, Lactobacillus brevis, Lactobacillus buchneri, Lactobacillus carnis, Lactobacillus casei, Lactobacillus catenaformis, Lactobacillus collinoides, Lactobacillus confusus, Lactobacillus coryniformis, Lactobacillus crispatus, Lactobacillus delbrueckii, Lactobacillus divergens, Lactobacillus farciminis, Lactobacillus fermentum, Lactobacillus fructivorans, Lactobacillus fructosus, Lactobacillus gasseri, Lactobacillus holotolerans, Lactobacillus hamsteri, Lactobacillus helveticus, Lactobacillus kefir, Lactobacillus lactis, Lactobacillus malefermentans, Lactobacillus mali, Lactobacillus minor, Lactobacillus minutus, Lactobacillus parabuchneri, Lactobacillus paracasei, Lactobacillus pentoaceticus, Lactobacillus plantarum, Lactobacillus reuteri, Lactobacillus ruminis, Lactobacillus sake, Lactobacillus salivarius, Lactobacillus xylosus, Lactococcus garviae, Lactococcus lactis, Lactococcus plantarum, Lactococcus raffinolactis, Corynebacterium accolens, Corynebacterium acetoacidophilum, Corynebacterium acetoglutamicum, Corynebacterium acnes, Corynebacterium alkanolyticum, Corynebacterium alkanum, Corynebacterium ammoniagenes, Corynebacterium amycolatum, Corynebacterium aquaticum, Corynebacterium aurantiacum, Corynebacterium barkeri, Corynebacterium callunae, Corynebacterium cystitidis, Corynebacterium dioxydans, Corynebacterium equi, Corynebacterium flaccumfaciens, Corynebacterium flavescens, Corynebacterium fujiokense, Corynebacterium glutamicum, Corynebacterium glycinophilum, Corynebacterium haemolyticum, Corynebacterium herculis, Corynebacterium histidiolovorans, Corynebacterium hoagii, Corynebacterium humiferum, Corynebacterium hydrocarboclastum, Corynebacterium hydrocarbooxydans, Corynebacterium insidiosum, Corynebacterium jeikeium, Corynebacterium kutscheri, Corynebacterium lilium, Corynebacterium liquefaciens, Corynebacterium matruchotii, Corynebacterium mediolanum, Corynebacterium melassecola, Corynebacterium minutissimum, Corynebacterium mycetoides, Corynebacterium nephridii, Corynebacterium nitrophilus, Corynebacterium paraldehydium, Corynebacterium paurometabolum, Corynebacterium petophilum, Corynebacterium pilosum, Corynebacterium primorioxydans, Corynebacterium*

*rubrum, Corynebacterium simplex, Corynebacterium striatum, Corynebacterium tuberculostrearicum, Corynebacterium variabilis, Corynebacterium vitarumen, Corynebacterium xerosis, Brevibacterium acetylicum, Brevibacterium albidum, Brevibacterium album, Brevibacterium alkanolyticum, Brevibacterium alkanophilum, Brevibacterium ammoniagenes, Brevibacterium butanicum, Brevibacterium casei, Brevibacterium cerinum, Brevibacterium citreum, Brevibacterium divericatum, Brevibacterium epidermidis, Brevibacterium flavum, Brevibacterium frigoritolerans, Brevibacterium fuscum, Brevibacterium glutamigenes, Brevibacterium halotolerans, Brevibacterium healii, Brevibacterium helvolum, Brevibacterium immariohilium, Brevibacterium imperiale, Brevibacterium incertum, Brevibacterium insectiphilium, Brevibacterium iodinum, Brevibacterium ketoglutamicum, Brevibacterium ketosoreductum, Brevibacterium lactofermentum, Brevibacterium linens, Brevibacterium luteum, Brevibacterium lyticum, Brevibacterium maris, Brevibacterium paraffinoliticum, Brevibacterium protophormiae, Brevibacterium pusillum, Brevibacterium roseum, Brevibacterium saccharolyticum, Brevibacterium saperdae, Brevibacterium seonmiso, Brevibacterium stationis, Brevibacterium sterolicum, Brevibacterium sulfureum, Brevibacterium taipei* or *Brevibacterium testaceum*; or plants such as soya, oilseed rape, flax, sunflowers or *Saccharomyces cerevisiae* are especially preferred, most preferred are *Brevibacterium ammoniagenes, Brevibacterium flavum, Brevibacterium ketoglutamicum, Brevibacterium iodinum, Brevibacterium lactofermentum, Brevibacterium linens, Brevibacterium saccharolyticum, Corynebacterium acetoglutamicum, Corynebacterium ammoniagenes, Corynebacterium glutamicum, Corynebacterium melassecola, Bifidobacterium breve, Bifidobacterium dentium* or *Bifidobacterium pseudocatenulatum*.

1. *Bifidobacterium*

The genus *Bifidobacterium* consists of about 30 species of gram-positive, anaerobic nonmotile, various shaped rods (Jay, 1996). They are non-spore forming, catalase-negative and non-acid fast. Cells often stain irregularly with methylene blue. Some species can tolerate $O_2$ in the presence of $CO_2$. Optimum growth temperature is 37–41° C. and optimal pH for initial growth is 6.5–7.0 (Bergey's Manual, 1989). *Bifidobacteria* produce acetic and lactic acid in the molar ratio of 3:2, and also a small amount of formic acid, ethanol and succinic acid. A unique characteristic of *bifidobacteria* is the glucose degradation pathway by the "fructose-6-phosphate shunt" using the enzyme fructose-6-phosphoketolase. As a nitrogen source, *bifidobacteria* can utilize ammonium. The G+C content of the DNA varies from 55–67 mol %. *Bifidobacteria* were first isolated from human infants' faeces (György, 1953), and are predominantly found in the intestines of humans and swine.

2. *Propionibacterium*

*Propionibacterium* species are small, pleomorphic rods of 0.5–0.8 m in diameter and 1–5 m in length, often with one end rounded and one pointed. The cells can be coccoid, bifid or branched and they appear singly, in pairs or in short chains in V or Y configurations or in "Chinese character" arrangements (Bergey's Manual, 1989). This genus are Gram-positive, non sporing chemoorganotrophs that are nonmotile. They are slow growing, requiring several days of incubation for visible signs of growth. They usually grow better anaerobically than aerobically at an optimum temperature of 30–37° C. (Cogan and Accolas, 1996). Fermentation products are large amounts of propionic and acetic acid, however, they also produce $CO_2$, which is responsible for the large eyes in Swiss cheese, formed during lactate fermentation, according to;

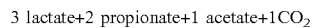

3 lactate+2 propionate+1 acetate+1$CO_2$

Propionibacteria are generally catalase-positive. The G+C content of their DNA varies from 53–67 mol %. Based on habitats, there are two principial groups of microorganisms, i.e. strains from cheese and dairy products and strains found on human skin or in the intestines.

Depending on the host organism, the organisms used in the processes are grown or cultured in the manner known to those skilled in the art. As a rule, microorganisms are grown in a liquid medium which contains a carbon source, usually in the form of sugars, a nitrogen source, usually in the form of organic nitrogen sources such as yeast extract or salts such as ammonium sulfate, a phosphate source such as potassium hydrogen phosphate, trace elements such as iron salts, manganese salts, magnesium salts and, if required, vitamins, at temperatures between 0° C. and 100° C., preferably between 10° C. and 60° C., more preferably between 15° C. and 50° C., while gassing in oxygen. The pH of the liquid medium can be maintained at a fixed value, i.e. the pH is regulated while culture takes place. The pH should then be in a range between pH 2 and pH 9. However, the microorganisms may also be cultured without pH regulation. Culturing can be effected by the batch method, the semi-batch method or continuously. Nutrients may be supplied at the beginning of the fermentation or fed in semicontinuously or continuously.

Post-transformation, plants are first regenerated and then grown or planted as usual.

After the organisms have been grown, the lipids are obtained in the usual manner. To this end, the organisms can first be harvested and then disrupted, or they can be used directly. It is advantageous to extract the lipids with suitable solvents such as apolar solvents, for example hexane, or polar solvents, for example ethanol, isopropanol, or mixtures such as hexane/isopropanol, phenol/chloroform/isoamyl alcohol, at temperatures between 0° C. and 80° C., preferably between 20° C. and 50° C. As a rule, the biomass is extracted with an excess of solvent, for example with an excess of solvent to biomass of 1:4. The solvent is subsequently removed, for example by distillation. The extraction may also be carried out with supercritical $CO_2$. After the extraction, the remainder of the biomass can be removed, for example, by filtration. Standard methods for the extraction of fatty acids from plants and microorganisms are described in Bligh et al. (Can. J. Biochem. Physiol. 37, 1959: 911–917) or Vick et al. (Plant Physiol. 69, 1982: 1103–1108).

The crude oil thus obtained can then be purified further, for example by removing cloudiness by adding polar solvents such as acetone or apolar solvents such as chloroform, followed by filtration or centrifugation. Further purification via columns or other techniques is also possible.

To obtain the free fatty acids from the triglycerides, the latter are hyrolyzed in the customary manner, for example using NaOH or KOH.

Another aspect of the invention is the production of conjugated linoleic acid by cultivating a microorganism of the genus *Bifidobacterium, Corynebacterium* or *Brevibacterium* in the presence of linoleic acid and isolating the formed conjugated linoleic acid.

In addition the invention furthermore relates to the use of microorganism of the genus *Bifidobacterium* as a probiotic in food and feed. Such use is in order to prevent or reduce the effects of diarrhoea, infections, cancer and antibiotic treatment.

The invention furthermore relates to conjugated unsaturated fatty acids and triglycerides with an increased content of conjugated unsaturated fatty acids which have been prepared by the abovementioned processes, and to their use for the preparation of foodstuffs, animal feed, cosmetics or pharmaceuticals. To this end, they are added to the foodstuffs, animal feed, cosmetics or pharmaceuticals in the customary quantities.

The invention is illustrated in greater detail in the examples which follow:

EXAMPLES

Nineteen strains of *Lactobacillus*, 2 strains of *Lactococcus*, 1 strain of *Pediococcus*, 4 strains of *Propionibacterium* and 23 strains of *Bifidobacterium* were screened for their ability to produce conjugated linoleic acid (CLA) from linoleic acid. Of these, 7 strains of *Bifidobacterium*, as well as 2 strains of *Propionibacterium* produced the cis-9, trans-11 CLA isomer from linoleic acid. In contrast, strains used of *Lactobacillus, Lactococcus* and *Pediococcus* lacked the ability to synthesise CLA. CLA (cis-9, trans-11 isomer) production by the genus *Bifidobacterium* was shown to exhibit considerable interspecies variation, with *B.breve* and *B.dentium* being the most efficient producers among the strains tested, yielding up to 65% conversion of linoleic acid to CLA at linoleic acid concentrations of 0.2–1.0 mg/ml in MRS medium. The growth of *B.breve* strains was inhibited by increasing concentrations of linoleic acid. Viability of *B.breve* 2257 was unaffected in the presence of up to 0.5 mg/ml linoleic acid for 48 h but was dramatically reduced to 1.5% survival at 1 mg/ml linoleic acid. However, viability of the *B.breve* strains NCFB2258, NCTC 11815, NCIMB 8815 and NCIMB 8807 was reduced to <60% at linoleic acid concentrations of 0.2 mg/ml. These data suggest that certain strains of *bifidobacteria* may have applications to elevate CLA content of food products and CLA status in humans.

Materials and Methods

Example 1

Maintenance of Bacterial Strains

The 19 strains of *Lactobacillus*, 2 strains of *Lactococcus*, 1 strain of *Pediococcus*, 4 strains of *Propionibacterium* and 19 strains of *Bifidobacterium* were used in this study.

Table 1 shows an example of the CLM production of certain strains tested.

TABLE 1

Screening of Propionibacterium strains for CLA production from linoleic acid in MRS media.

| Strain | Remaining LA (µg/ml) | CLA produced (µg/ml) |
|---|---|---|
| P. acidi propionici NCFB 5633 | 87.5 | — |
| P. freudenreichii spp. shermanii LMG 16424 | 73.0 | 12.1 |
| P. freudenreichii spp. shermanii JS (Visby) | 73.0 | 13.8 |

The *Lactobacilli, Pediococci* and *Bifidobacterium* strains were cultured in MRS (Difco Laboratories, Detroit, Mich., USA) under anaerobic conditions (anaerobic jars with 'Anaerocult A' gas packs; Merck, Darmstadt, Germany) and 1.5% (w/v): agar (Oxoid Ltd. Basingstoke, Hampshire, UK) was included for plating. *Pediococci, Lb.reuteri* NCIMB 702655, *Lb. reuteri* NCIMB 7025656 and *Lb. reuteri* DSM 20016 were routinely cultured at 30° C. and the remaining *Lactobacillus* strains were cultured at 37° C. for 24 h. For *Bifidobacterium,* 0.05% (w/v) L-cysteine hydrochloride (98% pure, Sigma Chemical Co. St. Louis, Mo., USA) was added to the medium and cultures were grown for 48 h at 37° C. under anaerobic conditions. *Lactococcus* strains were cultured in MRS under aerobic conditions at 30° C. for 24 h. The *Propionibacterium* strains were cultured in sodium lactate medium (SLM, Malik et al. 1968) at 20° C. for 72 h under anaerobic conditions. Total viable counts were determined by pour plating of 10-fold serial dilutions in Maximum Recovery Diluent (Oxoid), using MRS agar for *lactobacilli* and MRS agar with 0.05% (w/v) cysteine for *bifidobacteria*.

Example 2

Assay for Microbial CLA Production

Prior to examination of the strains for CLA production, each was subcultured twice in MRS broth (supplemented with cysteine, 0.05% w/v for *Bifidobacterium*) for 48 h, using a 1% innoculum. All strains were then cultured in MRS broth (supplemented with cysteine, 0.05% w/v for *Bifidobacterium*), spiked with different concentrations of free linoleic acid (LA: cis-9, cis-12-octadecadienoic acid, 99% pure, Sigma Chemical Co.). This was added as a 30 mg/ml stock solution of linoleic acid in 2% (v/v) Tween 80 (polyoxyethylene sorbitan mono-oleate; Merck-Schuchardt, Germany), which was previously sterile-filtered through a 0.45 µm Minisart filter (Sartφrius AG, Germany). The strains were inoculated to a density of $10^6$ cfu/ml in free linoleic acid-containing MRS media and incubated for their respective times and temperatures (described above). Following incubation, 5 ml of the cultures were centrifuged at 960×g for 5 min at room temperature (Sanyo MISTRAL 2000R Centrifuge).

The fatty acid composition of the resulting supernatant was analysed as follows. Initially, $C_{13:0}$ (tridecanoic acid, 99% pure, Sigma Chemical Co.) was added to 4 ml of the resulting supernatant, as an internal standard at a concentration of 0.25× the initial linoleic acid concentration and lipid extraction was performed as follows. Two milliliters of isopropanol (99% purity, Alkem Chemicals Ltd., Cork, Ireland) was added to the supernatant and the samples were vortexed for 30 sec. A total of 4.5 ml hexane (99%. purity, LabScan Ltd., Dublin, Ireland) was added to this and the mixture plased on a shaking platform for 3 min before centrifugation at 960×g for 5 min at room temperature. The supernatant (the hexane layer containing the lipids) was removed and the procedure was repeated twice. The hexane layers were pooled and stored at −20° C. prior to preparation of fatty acid methyl esters (FAME) for gas liquid chromatographic (GLC) analysis.

Example 3

Preparation of Fatty Acid Methyl Esters (FAME) and GLC Analysis

The lipid extracts in hexane were analysed by GLC following acid-catalyzed methylation as described previously (Stanton et al., 1997). Free fatty acids in oils such as sunflower and soybean oils were calculated as the difference between fatty acid concentrations obtained following acid and base catalyzed methylation, performed using 2 N methanolic KOH (Sigma Chemical Co.) at room temperature.

The GLC was performed with reference to the internal standard $C_{13:0}$. Separation of the FAME was performed on a Chrompack CP Sil 88 column (Chrompack, Middleburg, The Netherlands, 100 m×0.25 mm i.d., 0.20 μm film thickness), using helium as carrier gas at a pressure of 37 psi. The injector temperature was held isothermally at 225° C. for 10 min and the detector temperature was 250° C. The column oven was held at an initial temperature of 140° C. for 8 min and then programmed at an increase of 8.5° C./min to a final temperature of 200° C., which was held for 41 min. Collected data were recorded and analyzed on a Minichrom PC system (VG Data System, Manchester, UK). The cis-9, trans-11 CLA isomer was identified by retention time with reference to a CLA mix (Nu-Chek-Prep. Inc., Elysian, Minn.). The percentage conversion to CLA and the remaining linoleic acid in the broth were calculated by dividing the amount of CLA and linoleic acid present in the broth after inoculation and incubation with the various cultures used with the amount of linoleic acid present in the spiked broth before incubation.

Example 4

CLA Production by B.Breve NCFB 2258 Using triglyceride Bound Linoleic Acid as Substrate B.breve NCFB 2258 was further investigated for ability to utilise triglyceride bound linoleic acid as substrate for CLA production. B.breve NCFB 2258 was inoculated from a fully grown culture into MRS broth with added cysteine (0.05%) and trilinolein ($C_{18:2}$, cis-9, cis-12, 99% pure, Sigma Chemical Co.), soybean oil and sunflower oil (purchased from a local grocery store) containing known linoleic acid concentrations. The triglyceride mixtures were sterile-filtered through 0.45 μm Minsart filters and added as 5 mg/ml aqueous solutions in 2.5% (v/v) Tween 80. Substantial vortexing was required to dissolve the fat particles. The volume of the triglyceride stock solutions added was calculated to give a final concentration of 0.2 mg linoleic acid/ml of broth. B.breve 2258 was inoculated into MRS broth in the presence of the triglyceride substrates under anaerobic conditions at 37° C. and incubated for 48 h.

Additional Examples

Strains used in this study included Bifidobacterium breve 2258, which was obtained from NCIMB (National Collection of Industrial and Marine Bacteria, Aberdeen, Scotland) and Propionibacterium freudenreichii shermanii 9093 (PFS), which was obtained from Kemikalia AB, Lund, Sweden.

The bifidobacteria strain, B.breve 2258, used in this study was cultured in MRS media (pH 6.0) (Oxoid Ltd, Hampshire, UK) with 1.5% (w/v) agar (Oxoid Ltd, Hampshire, UK) and 0.05% (w/v) L-cysteine hydrocloride (Sigma Chemical, 98% pure) under anaerobic conditions using anaerobic jars with 'Anaerocult A' gas packs (Merck, Darmstadt, Germany). The cultures were grown for 72 h at 37° C. and then subcultured (restroke from a singe colony) for pure colonies.

The strain of propionibacteria, P.freudenreichii shermanii, 9093 (PFS), used in this study was cultured in sodium lactate medium (SLM), pH 7.0 (Malik et al., 1968) at 30° C. for 72 h under anaerobic conditions and then subcultured for purity.

Example 5

Screening Assay for Microbial CLA Production from Linoleic Acid

After subculturing twice, strains B.breve 2258 and P. freudenreichii shermanii 9093 were cultured in MRS broth containing 0.05% cysteine (w/v) and SLM, respectively, for 24 h (bifidobacteria) and 48 h (propionibacteria). A 1% (v/v) inoculum was then transferred to new broth tubes containing 0.5 mg/ml linoleic acid (LA) (Sigma Chemical Co. St. Louis, Mo., USA, 99% pure), added as 30 mg/ml stock solution in 2% (v/v) Tween 80 (polyoxyethylene sorbitan mono-oleate) (Merck-Schuchardt, Germany) which was sterile filtered through 0.45 m Minisart filter (Sartrius AG, Germany) and stored in the dark at −20° C. The cultures were then grown for 48 h (bifidobacteria) and 72 h (propionibacteria) at their respective temperatures, prior to lipid extraction of both supernatant and bacterial pellets. All extractions were performed in duplicate and control cultures were incubated in the absence of added fatty acids.

Example 6

Screening Assay for Microbial Biohydrogenation of CLA

After subculturing twice, both strains were cultured in their respective media for 24 h (bifidobacteria) and 48 h (propionibacteria), and then a 1% (v/v) inoculum was transferred to new broth tubes, containing 0.5 mg/ml pure cis-9, trans-11 CLA (Matreya Inc. Pa., USA). The CLA was added as a 30 mg/ml stock solution in 2% (v/v) Tween 80, which was sterile filtered. The cultures were grown for 48 h (bifidobacteria) and 72 h (propionibacteria) at their respective temperatures, followed by lipid extraction of both supernatant and bacterial pellets. All extractions were performed in duplicate and control cultures were incubated in the absence of added fatty acids.

Example 7

Lipid Extraction of Supernatant

After transferring 10 ml of the cultures inoculated with either CLA or LA to 15 ml centrifuge tubes (Sarstedt, Numbrecht, Germany), centrifugation was performed at 2197×g for 20 min at room temperature (20C), using a Sanyo Mistral 2000 R centrifuge. To 4 ml of the supernatant were added 0.75 mg C 13:0 (tridecenoic acid, Sigma, 99% pure) as internal standard prior to lipid extraction, performed as follows: 2 ml isopropanol (Alkem Chemicals Ltd. Cork, Ireland, 99% purity) and 1.5 ml hexane (LabScan Ltd. Dublin, Ireland, 99% purity) were added to the supernatant and vortex mixed, and a further 3 ml of hexane were then added and the mixture, which was vortex mixed again before centrifugation at 2197×g for 5 min. All upper layer (hexane layer containing fatty acids) was transferred to a screw capped glass tube and dried down under $N_2$ gas stream. Tubes were then stored at −20° C. prior to preparation of fatty acid methyl esters (FAME) for GLC (Gas Liquid Chromatography) analysis. Following GLC, results were calculated as mg fatty acid per ml of broth.

Example 8

Lipid Extraction of Pellet

After removal of supernatant, bacterial cells (pellets) from 10 ml of grown culture were washed by adding and resuspending them in 1 ml saline solution (0.137 M NaCl, 7.0 mM $K_2HPO_4$, 2.5 mM $KH_2PO_4$) and vortex mixing before centrifuging at 3632×g for 30 min. After removal of supernatant, pellets were again resuspended in 1 ml saline solution followed by centrifugation at 3632×g for 15 min and removal of the supernatant again. The cells were again resuspended in 1 ml saline solution, to which was added 0.75 mg C 13:0 (as described above for supernatant) as internal standard prior to preparation of FAME for GLC analysis. Following GLC, results were calculated as mg fatty acids from 1 ml of fully grown culture and expressed as mg fatty acids/ml.

Example 9

Preparation of Fatty Acid Methyl Esters (FAME)

Acid catalyzed methylation, which results in derivatisation of both free fatty acids and triglyceride bound fatty acids was performed as described below: Extracted lipids from supernatants and pellets (as described in sections 2.4.1 and 2.4.2) in screw capped glass tube, were resuspended in 12 ml, 4% methanolic HCl (v/v) (Supelco Inc. Bellefonte, Pa., USA) in methanol and vortex mixed for 10 sec. The lipids in methanolic HCl were incubated at 60° C. for 1 h with vortex mixing every 10 min. Two ml of water saturated with hexane and 5 ml of hexane were then added to the solution which was vortex mixed for 30 sec, and then allowed to stand for 30 min. The clear top layer, containing the FAME was subsequently transferred to a tube and 2 ml of water saturated with hexane were added and the solution again vortex mixed and allowed to stand for 30 min. Following this, the top layer was transferred to a new tube and the methylation reaction terminated by addition to this layer of 0.5 g anhydrous sodium sulphate (Sigma, 99% purity) and vortex mixed for 5 sec. After 1 h, the top layer was removed and stored at −20° C. prior to GLC analysis.

Example 10

GLC Analysis

The free fatty acids were analysed as fatty acid methyl esters (FAME) using a gas liquid chromatograph (GLC-Varian 3400, Varian, Harbor City, Calif., USA) fitted with a flame ionization detector (FID) and a Septun Programmable Injector (SPI). Quantification of fatty acids was performed with reference to the internal standard (C 13:0). Separation of fatty acids was performed on a Chrompack CP Sil 88 column (Chrompack, Middleburg, The Netherlands) (100 m×0.25 mm i.d., 0.20 m film thickness), using He as carrier gas at a pressure of 33 psi. The injector temperature was held isothermally at 225° C. for 10 min and the detector temperature was 250° C. The column oven was held at an initial temperature of 140° C. for 8 min, and then programmed at an increase of 8.5 C/min to a final temperature of 200° C., which was held for 41 min.

Collected data were recorded and analyzed on a Minichrom PC system (VG Data System, Manchester, UK). The cis-9, trans-11 CLA isomer was identified by retention time with reference to CLA standards (Matreya Inc. Pa., USA), and trans-11-C 18:1 and stearic acid (Sigma Chemical Co. St. Louis, Mo., USA) identified by reference to their standard fatty acids. To calculate correction factors for the CLA isomer peaks the internal standard C 13:0 was used using the following formula: $Cf_I=(A_{IS} \times Wt_I)/(A_I \times Wt_{IS})$, where $Cf_I$ is the correction factor for the actual CLA isomer, $A_{IS}$ is refers to the area of the internal standard (C 13:0), $A_I$ is the area of the CLA peak, $Wt_I$ is the weight of the CLA isomer and $Wt_{IS}$ refers to the weight of the internal standard. The quantity of CLA was expressed as mg/ml broth, and throughout the thesis CLA refers to the cis-9, trans-11 isomer (unless otherwise stated), which was the most abundant CLA isomer formed during microbial biohydrogenation of free linoleic acid. The response factors of the individual fatty acids were calculated relative to the area of C 18:0, which was assigned a response factor of 1.00. The % conversion to CLA and the % remaining linoleic acid in the broth were calculated by dividing the amount of CLA and linoleic acid present in the broth after inoculation with the cultures used, with the amount of linoleic acid present in the spiked broth before incubation.

Example 11

DNA Sequence Analysis

The sequence encoding the putative linoleic acid isomerase gene from *Lactobacillus reuteri* (Rosson, et al., 1999, WO 99/32604) was compared to sequence databases (GenBank+unfinished genomes databases), using the BLAST suite of programs (Altschul et al., 1990). Proteins exhibiting significant similarity were aligned using DNAStar software (DNAStar Inc. Madison, Wisc.) and conserved motifs were identified. Degenerate oligonucleotide primers, specific for these motifs, were designed and used in PCR reactions. For each primer, one general and one specific primer were designed (codon usage of the strains were taken under consideration when designing the specific primers). Primers were designed as follows (all sequences are written 5'–3'):

```
Primer 1 (amino acid sequence):     G  N  Y  E  A  F  A 1a      (general):                  GGI, AA(C/T), TA(C/T), GA(A/G), GCI, TT(T/C), GA(A/G).

1b      (specific for bifidobacteria): GGI, AAC, TAC, GAA, GCI, TTC, GAA

Primer 2 (amino acid sequence):     R  G  G  R  E  M  E  N  H  F  E  C 2a      (general):                  CGI, GGI, GGI, CGI, GA(A/G), ATG, GA(A/G), AA(C/T),
                                    CA(C/T), TT(C/T), GA(A/G), TG(C/T).

2b      (spec. for bif.):           CGI, GGI, CGI, GAA, ATG, GAA, AAC, CA(C/T), TTC,
                                    GAA, TGC.
```

-continued

| | | |
|---|---|---|
| Primer 3 (amino acid sequence): | Y W X T M F A F E | |
| 3a | (general): | TA(C/T), TGG, III, ACI, ATG, TT(C/T), GCI, TT(C/T), GA(A/G). |
| 3b | (spec, for bif.): | TAC, TGG, III, ACC, ATG, TTC, GCI, TTC, GAA. |
| Primer 4 (amino acid sequence): | Y W X T M F A F E | |
| 4a | (general): | TC, (G/A)AA, IGC, (A/G)AA, CAT, IGT, III, CCA, (A/G)TA. |
| 4b | (spec. for bif.): | TTC, GAA, IGC, GAA, CAT, GGT, III, CCA, GTA. |
| Primer 5 (amino acid sequence): | D T V F T T E Y S | |
| 5a | (general): | GA, GA(T/A), (T/C)TC, IGT, IGT, (G/A)AA, IAC, IGT, (G/A)TC. |
| 5b | (spec. for bif.): | GA, GTA, TTC, (G/A)GT, (G/A)GT, GAA, GAC, (G/A)GT, (G/A)TC. |
| Primer 6 (amino acid sequence): | T A M E A V Y | |
| 6a | (general): | TA, IAC, IGC, (T/C)TC, CAT, IGC, IGT. |
| 6b | (spec, for bif.): | GTA, (G/C)AC, IGC, TTC, CAT, IGC, (G/A)GT. |

Example 12

Chromosomal DNA Isolation

Genomic DNA from *B.breve* 2258 and *P.freudenreichii shermani* 9093 (PFS) was isolated from 1.5 ml of an overnight broth culture using a modification of the method of Hoffman and Winston (1987). The cells were lysed with glass beads using the procedure as described by Coakley et al. (1996). The DNA pellet was dried at 37° C. in a heating block, resuspended in 50 l sterile destined water and stored at −20° C. Aliquots of 2 μl of extracted DNA were subsequently used in 50 μl PCR reactions.

Example 13

PCR Analysis

PCR amplifications were performed in a total volume of 50 l in a Hybaid PCR Express Unit (Hybaid Ltd. Middlesex, UK), with an annealing temperature of 45° C. Each reaction contained 1 μl of each primer (50 pmol/l), 2 μl of template in 5 μl MgCl$_2$ (50 mM), 5 μl dNTP Master Mix (12.5 mM), 5 μl 10×NH$_4$ Reaction Buffer and 0.5 μl Biotaq DNA Polymerase (5 u/l) (BIOLINE, London, UK). The resulting amplified 1 kb DNA fragment was then cloned into a vector, as described in example 17 (FIG. 4).

Example 14

Chromosome Walking by Inverse PCR

Having confirmed, by comparison of the sequence of the PCR fragment to the known sequence of linoleic acid isomerase of *Lb. reuteri*, that the flanking 5' and 3' ends of the putative linoleic acid isomerase were missing the following strategy was followed. The strategy to obtain flanking chromosomal sequence involved the use of two primers, designed to terminal regions of the known chromosomal DNA sequence (FIG. 3). The genomic DNA from *B.breve* 2258 and *P. freudenreichii shermanii* 9093 were digested with different restriction enzymes followed by ligation with DNA ligase (1 μl in 50 μl reactions, 400 u/ml, New England BioLabs Inc. Hertfordshire, UK). This was then subsequently used as a template in the inverse PCR reactions with the terminal primers. The reactions were set up the same way as the standard PCR reactions but with an annealing temperature of 50° C. and the resulting fragment (analysed after separation by agarose gel electrophoresis, described in example 16) was cloned into the PCR2.1-TOPO, vector, as described in example 17 (FIG. 4). The two terminal primers used were:

```
Primer A (upstream):
3' CGTTCTCGACCTTGGTGTTGTATCGGAATT 5'.

Primer B (downstream):
5' GTACCGACCGACAAGATCGAGTCGCTTGCC 3'.
```

Example 15

Chromosome Walking Using a Single Primer

From the approach described above, it was confirmed that the 3' end of the gene was sequenced, but however, the 5' end was not obtained. A second approach for obtaining the 5' end of the gene, PCR walking involved the use of just a single primer designed to the 5' end of the sequenced chrosomal DNA. It was hoped that the primer would bind to this 5' side upstream of the gene and to various sites (at low annealing temp.), which would generate a number of fragments after PCR amplification. PCR reactions were carried out in a gradient PCR (Stratagene RoboCycler Gradient 96), at 37–50° C. annealing temperatures. Two reactions (40° C. and 50° C. annealing temp.), each generating a few fragments as evidenced by a small number of bands on an agarose gel (described in example 16) were chosen for cloning, as described in example 17.

Example 16

Analysis of PCR Products by Agarose Gel Electrophoresis

Two microlitres of loading dye was added to 10 μl of each PCR product and loaded on a 1.5% (w/v) agarose (Sigma Chemical CO. St. Louis, Mo., USA) gel. This DNA was then separated by gel electrophoresis at 100 V for 2 h. Gels were stained with ethidium bromide (200 ng/ml in 1× TAE buffer) and PCR products were visualized by UV transillumination.

Example 17

Cloning

Selected PCR fragments based on the genomes of both *B.breve* 2258 and *P.freudenreichii shermanii* 9093, were cloned into the vector (pCR2.1-TOPO, Invitrogen BV, Groningen, The Netherlands) which was transformed, by heat shocking, into competent *E.coli* cells according to the manufacturers' instructions (Invitrogen BV, Groningen, The Netherlands). Recombinants (white colonies) were selected on LB agar supplemented with 40 µl 5-bromo-4-chloro-3-indolyl-D-galacto-sidase (X-Gal; 40 mg/ml). DNA extraction was performed using QIAGEN Plasmid Mini Kit (QIAGEN, Inc., Chatsworth, Calif., USA). Confirmation that the cloning was successful was achieved by digestion with the restriction enzyme, Eco R1, which has restriction sites within the multiple cloning site. (FIG. 3 and FIG. 4).

Example 18

Assay other Bifidobacterial Strains for 1 kb PCR Fragment

After obtaining sequencing results of the 1 kb PCR fragment from *B.breve* 2258 and *P.freudenreichii shermanii* 9093, which confirmed that both fragments exhibited significant similarity to the linoleic acid isomerase gene sequence of *Lb. reuteri*, the genomic DNA from a range of strains of *bifidobacteria* (previously isolated as described in example 11) was screened (Table 2) for the presence of a similar gene using primers 3 (general) and 5 (general) in PCR reactions performed as previously described (example 13). The following strains were screened:

Table 2 Strains screened for the presence of the gene encoding linoleic acid isomerase using the primers 5 (general) and 3 (general) designed based on the sequence of the gene linoleic acid isomerase from *Lb. reuteri*.

| Species | Strain | Source | Growth in 0.5 mg/ml | CLA prod. |
|---|---|---|---|---|
| B. adolescentis | NCFB 2204 | Adult intestine | + | 0 |
| B. breve | NCFB 2257 | Infant intestine | + | ++ |
| B. breve | NCFB 2258 | Infant intestine | + | +++ |
| B. breve | NCIMB 8815 | Nursling stools | + | +++ |
| B. dentium | NCFB 2243 | Dental carries | + | +++ |
| B. infantis | NCFB 2205 | Infant intestine | + | 0 |
| B. lactis | Bb 12 | Chr. Hansens | + | 0 |
| B. longum | NCFB 2259 | Adult intestine | + | 0 |
| B. longum | BB 536 | Visby | + | 0 |

+++: >60 µg CLA/ml broth
++: >15 µg CLA/ml broth
+: >5 µg CLA/ml broth, growth
: no CLA produced, no growth The PCR products obtained following PCR reactions were analyzed by agarose gel electrophoresis, as previously described (example 16).

Results and Discussion

1. CLA Production by Bacterial Strains

Throughout the screening programme, the two *Propionibacterium* strains, *Propionibacterium freudenreichii* subsp. *freudenreichii* Propioni 6 (PFF-6) and *Propionibacterium freudenreichii* spp. *shermanii* 9093 (PFS), previously reported to synthesise CLA from linoleic acid (Jiang et al., 1998) were used as positive controls. The CLA biosynthetic assay was set up, with the positive controls in SLM broth, using similar incubation conditions as described previously (Jiang et al., 1998). GLC analysis confirmed that the two strains did convert free linoleic acid to the cis-9, trans-11 CLA isomer following incubation at 20° C. for 72 h, using CRM (certified reference material) 164 and CIA standards for fatty acid identification (data not shown). However, the levels of CLA produced by the two strains of *Propionibacterium* were lower than that reported previously by Jiang et al. (1998), producing ~60 µg/ml of CLA in comparison with 111.8 µg/ml previously reported by Jiang et al. (1998), using 0.5 mg/ml linoleic acid as substrate. In addition, we found that the amount of linoleic acid remaining in the media following incubation with the PFS strain was ~50 µg/ml, compared with 289.5 µg/ml reported previously (Jiang et al., 1998). The variation in these data may be a result of differences in the numbers of cells present during incubation, and possibly as a result of the different procedures used for fatty acid extraction and methylation.

Three strains of *Propionibacterium* were then examined for their ability to produce CLA. These were *Propionibacterium acidi propionici* NCFB 5633, *Propionibacterium freudenreichii* spp. *shermanii* LMG 16424 and *Propionibacterium freudenreichii* spp. *shermanii* JS (Laboratorium Visby, Tonder, Denmark). The strains were incubated in the presence of 0.5 mg/ml linoleic acid using the same growth conditions and media as described above. The two *Propionibacterium shermanii* strains synthesized CLA in MRS media while *Propionibacterium acidi propionici* did not produce any detectable CLA product (Table 1). The amounts of CLA produced by the two *Propionibacterium shermanii* strains (12–14 µg/ml) were low however, compared with 60 µg/ml produced by PFS strain in this study.

2. Screening of *Lactobacilli*, *Lactococci*, and *Pediococci* for CLA Production A variety of different strains of *lactobacilli*, *lactococci*, and *pediococci*, obtained from various sources (Table 3) were tested for ability to produce CLA from linoleic acid. These strains included a number of probiotic strains including five strains of *Lb.reuteri* and the *bacteriocin* producing *Lactcoccus lactis* DPC 3147 strain (Ryan et al., 1996). The strains were inoculated into MRS to a density of ~$10^6$ cfu/ml and incubated under respective conditions as described above, in the presence of linoleic acid concentrations of 0.5 to 3.0 mg/ml.

The ability of the strains to grow in the different linoleic acid concentrations varied considerably. Good growth of all five *Lb.reuterii* strains occurred at linoleic acid concentrations up to 1 mg/ml, while at 3 mg/ml, the growth of strains NCIMB 701359 and NCIMB 70256 was completely inhibited (data not shown). At all linoleic acid concentrations investigated, none of the *Lb.reuteri* strains investigated produced CLA in detectable quantities. *Lactobacillus helveticus* NCDO 1244 exhibited no growth in 0.5 mg/ml linoleic acid while *Lactobacillus leichmanii* NCDO 302 showed good growth in the presence of high linoleic acid concetrations (3 mg/ml). However, none of the strains produced CLA from linoleic acid (between 0.5 to 3 mg/ml) under the conditions used.

TABLE 3

Strains screened for CLA production

| Species | Code | Source |
|---|---|---|
| Lactobacillus reuteri | NCIMB 11951 | Adult intestine |
| Lactobacillus reuteri | NCIMB 701359 | Unknown |
| Lactobacillus reuteri | NCIMB 701089 | Unknown |
| Lactobacillus reuteri | NCIMB 702655 | From rat |
| Lactobacillus reuteri | NCIMB 702656 | From rat |
| Lactobacillus reuteri | DSM 20016 | |
| Lactobacillus helveticus | NCDO 257 | |
| Lactobacillus helveticus | ATCC 15009 | |
| Lactobacillus helveticus | NCDO 1244 | |
| Lactobacillus leichmanii | NCDO 299 | |
| Lactobacillus leichmanii | NCDO 302 | |
| Lactobacillus fermenticum | ATCC 338 | |
| Lactobacillus acidophilus | ATCC 4356 | |
| Lactobacillus | DPC 5336 | from cracker Barrel |
| Bifidobacterium breve | NCTC 11815 | |
| Lactcoccus lactis | DPC 3147 | |
| Lactococcus lactis 290P | DPC 152 | |
| Pediococcus pentasescus | FBB 63 | |

3. CLA Production from Linoleic Acid Among *Bifidobacterium* Strains Cultured in MRS A variety of bifidobacteria obtained from a number of sources (Table 4) were screened for CLA production. Since free linoleic acid was found to be inhibitory to the growth of bifidobacteria strains, the minimum inhibitory concentration of linoleic acid for the *B.breve* strains was initially determined. This involved inoculation (1% from grown cultures) of the *Bifidobacterium* strains into MRS containing free linoleic acid concentrations ranging from 0.2 to 1.5 mg/ml and incubation under anaerobic conditions at 37° C. for 48 h. The pH of the media remained unchanged following the addition of the linoleic acid substrate in this concentration range at pH~6.1. Viable bifidobacteria were enumerated at time zero and following 48 h incubation in the presence of the linoleic acid substrate. Viability of *B.breve* 2257 was unaffecetd in the presence of linoleic acid, at concentrations up to 0.5 mg/ml. However, viability was dramatically reduced at 1.0 mg/ml and only 1.5% survival was observed. In contrast the survival of strains *B.breve* 2258, 8807, 8815 and 11815 was reduced to <60% at linoleic acid concentrations of 0.2 mg/ml and higher. The bifidobacteria strains were then screened for CLA production from linoleic acid substrate at a concentration of 0.5 mg/ml, using the incubation conditions described above. A number of the *Bifidobacterium* strains investigated produced CLA following incubation in MRS containing 0.5 mg/ml linoleic acid, and the results from this screening program showed that there was considerable interspecies variation in the ability of bifidobacteria to produce CLA (Table 4).

TABLE 4

Conversion to CLA by *Bifidobacterium* strains cultured in MRS broth containing cysteine spiked with 0.5 mg/ml linoleic acid for 48 h.

| Species prod. | Strain | Source | Growth in 0.5 mg/ml | CLA |
|---|---|---|---|---|
| B. aolescentis | NCFB 2204 | Adult intestine | +[1] | 0 |
| B. adolescentis | NCFB 2230 | Adult intestine | 0[2] | −[3] |
| B. adolescentis | NCFB 2231 | Adult intestine | + | 0[4] |
| B. angulatum | NCFB 2236 | Human faeces | + | 0 |
| B. bifidum | NCFB 795 | Human milk | + | 0 |
| B. breve | NCFB 2257 | Infant intestine | + | ++ |
| B. breve | NCFB 2258 | Infant intestine | + | +++[7] |
| B. breve | NCTC 11815 | Infant intestine | + | +++ |
| B. breve | NCIMB 8815 | Nursing stools | + | +++ |
| B. breve | NCIMB 8807 | Nursing stools | + | +++ |
| B. dentium | NCFB 2243 | Dental carries | + | +++ |
| B. infantis | NCFB 2205 | Infant intestine | + | 0 |
| B. infantis | NCFB 2256 | Infant intestine | + | 0 |
| B. lactis | Bb12 | Chr. Hansens | + | 0 |
| B. longum | BB536 | Visby | + | 0 |
| B. pseudocatenulatum | NCIMB 8811 | Nursling stools | + | + |

[1] growth
[2] no growth
[3] not determined
[4] no CLA produced
5. >5 μg/ml CLA
6. >15 μg/ml CLA
[7] >60 μg/ml of broth All 5 strains of *Bifidobacterium* breve species examined tested positive for CLA production with four of these strains producing more than 60 μg/ml CLA, while strain *B.breve* NCFB 2257 produced 15 μg/ml under these conditions. In addition, *B.dentium* NCFB 2243 was an efficient CLA producer, also yielding >60 μg/mg CLA (Table 4), while *B.pseudocatenulatum* NCIMB 8811 produced >15 μg/ml under the experimental conditions employed. Among the other bifidobacteria species investigated, 3 strains of *B.adolescentis*, 2 strains of *B.longum* and 1 strain each of *B.angulatum*, *B.bifidum* and *B.lactis* were all negative for CLA production (Table 4). The exact role of biohydrogenation in the metabolic environment of the bacterial cell is unclear. In the study by Jiang et al. (1998), strains which were able to produce CLA were those inhibited by the presence of free linoleic acid, but a positive correlation between CLA production and tolerance to linoleic acid was observed within the three CLA producing strains of *propionibacteria*. This suggests that the conversion of linoleic acid to CLA is a detoxification mechanism for the bacterial cell. This is supported by the fact that the anti-microbial activity of fatty acids with double bonds of cis configuration is stronger than that of trans (Kabara, 1983).

The most efficient CLA producers were strains *B. breve* 8815 and 2258 at linoleic acid concentration of 1.0 mg/ml. The strains *B. breve* 8815, 2258 and 2257 were present at less than $10^4$ cells/ml at the highest linoleic acid concentration (1.5 mg/ml) and were not analysed for CLA conversion. *B.breve* NCFB 2258 converted ~50% of the added linoleic acid to CLA at 0.2 and 0.5 mg/ml linoleic acid concentrations. The ability of *B.breve* NCFB 2258 strain to utilise triglyceride bound linoleic acid as substrate for CLA production, using trilinolein. ($C_{18:2}$, cis-9, cis-12), sunflower and soybean oils was also investigated. The *B.breve* NCFB 2258 strain was found to be negative for ability to utilise triglyceride bound linoleic acid as substrate at 0.2 mg/ml linoleic acid for CLA production (data not shown), from trilinolein, sunflower and soybean oils. These data are in agreement with a previous study which showed that of 61 rumen isolates with ability to produce CLA, none utilised triglyceride bound linoleic acid (Fujimoto et al., 1993). In addition, trilinolein did not inhibit the growth of B.breve 2258 to the same extent as similar concentrations of free linoleic acid (data not shown). This indicates that linoleic acid in the free fatty acid form is more toxic to bifidobacteria than triglyceride-bound linoleic acid.

4. Microbial Biohydrogenation of Unsaturated C 18 Fatty Acids

B.breve 2258 and P.freudenreichii shermanii 9093 were screened for their ability to produce CLA. The strains were incubated in duplicate in the presence of 0.5 mg/ml linoleic acid (LA) and CLA (the pure cis-9, trans-11 isomer), respectively, using the same growth conditions and media as described. In order to compare the fatty acid composition, control cultures without added LA and CLA were also incubated using the same conditions. The propionibacteria strain used in this study was previously reported to synthezise CLA from LA (Jiang et al., 1998) and therefore used as a positive control. However, in this study, that result was not reproducible since the strain was clearly inhibited in the presence of LA and CLA and hence grew very poorly. No CLA production from that strain was therefore detected and the results from the GLC analysis are not presented here.

After separation (by centrifugation) of B.breve 2258 cells from the supernatant following incubation for 48 h, followed by lipid extraction and methylation, the fatty acid composition of both the cells (pellets) and the supernatant were analysed using GLC (example 10).

5. Change in Supernatant Fatty Acid Composition Following Incubation of B.breve 2258 with 0.5 mg/ml LA GLC analysis confirmed that B.breve 2258 converted LA to CLA. Of the added 0.5 mg/ml, only 0.27 mg/ml (54%) remained in the supernatant (FIG. 5), while the remainder (46%) was converted to other fatty acids, preferentially the cis-9, trans-11 CLA isomer followed by cis-9-C 18:1 (oleic acid) and a peak identified as trans-9, trans-11-CLA. The amount of cis-9, trans-11 CLA produced was 0.136 mg/ml, and trans-9, trans-11-CLA accounted for 0.03 mg/ml. The amount of these two fatty acids present in the control supernatant was negligible (FIG. 5) There was also a substantial increase of cis-9-C 18:1 (oleic acid) (64.8% compared with the control supernatant), which indicates that B.breve 2258 harbours a CLA reductase enzyme that hydrogenates the trans-11 double bond of cis-9, trans-11 CLA. Compared to the control culture there was 64,8% more stearic acid in the LA added supernatant. Smaller increases were observed also in the concentrations of trans-11 C 18:1 (vaccenic acid) (30.3%) and C 18:0 (stearic acid) (17.5%) compared with the control supernatant, suggesting that other hydrogenating enzymes may be involved.

6. Change in Membrane Fatty Acid Composition Following Incubation of B. breve 2258 with 0.5 mg/ml LA The fatty acid composition of the membranes from the cultures (pellet) grown in MRS medium with 0.5 mg/ml LA was also analysed and compared with the control cultures (FIG. 9). Results are expressed as mg fatty acids from cells/ml fully grown culture. The fatty acid concentration in the pellets in mg/ml is lower than that of the supernatant and therefore are not directly comparable. Results from the GLC analysis show that CLA was incorporated in the cell membranes, whereas the control culture contained negligible CLA. The cis-9, trans-11 isomer was the most abundant CLA isomer and accounted for 0.012 mg/ml, which represents 70% of the total CLA isomers. The content of the cis-9-C 18:1 (oleic acid) was increased (by 271% compared with controls) in the membranes of B.breve 2258 cells incubated in LA (0.5 mg/ml), indicating the presence of a CLA reductase, which was capable of reducing the unsaturated trans-11 bond in CLA in B.breve 2258. The trans-11 C 18:1 (vaccenic acid) content of the cell membranes wes reduced (over 4-fold) in the LA treated cells compared with the control cells. As seen in the supernatant, a small increase of 28% in C 18:0 (stearic acid) was detected in the membranes of the LA treated cells compared with the controls (FIG. 9).

7. Change in Supernatant Fatty Acid Composition Following Incubation of B.breve 2258 with 0.5 mg/ml cis-9, trans-11 CLA In order to evaluate if B.breve 2258 possesses enzymes other than the putative linoleic acid isomerase, involved in the biohydrogenation of linoleic acid, studies were undertaken using cis-9, trans-11 CLA as the substrate. Strain B.breve 2258 was inoculated in MRS containing 0.5 mg/ml of the pure cis-9, trans-11 CLA isomer (Matreya Inc. PA, USA) and incubated for 24 h at 37° C. Following incubation in the presence CLA (0.5 mg/ml), only 0.32 mg/ml (65%) remained in the supernatant (FIG. 9) with the remaining 35% converted to other fatty acids. The most predominantly formed fatty acid corresponded to trans-9, trans-11-CLA, observed following incubation with LA and eluted at 43 mins (FIGS. 6 and 10). This CLA isomer was present at 0.12 mg/ml (71% of the cis-9, trans-11 CLA peak). Oleic acid was also formed in the supernatant by B.breve 2258 following incubation with cis-9, trans-11 CLA with an increase of 85.5% compared with the control supernatant. Smaller increases were also observed in the concentration of trans-11-C 18:1 (vaccenic acid) (74.5% compared to control.supernatant) and C 18:0 (stearic acid) (23.9% compared to control supernatant).

8. Change in Membrane Fatty Acid Composition Following Incubation of B.breve 2258 with 0.5 mg/ml cis-9, trans-11 CLA The lipid composition of the membrane following incubation of B.breve 2258 in cis-9, trans-11 CLA was also compared with control cells incubated in the absence of CLA. The fatty acid composition of the membranes from cultures inoculated in MRS containing 0.5 mg/ml of the pure cis-9, trans-11 CLA isomer shows that the membrane composition changed compared with the control. Cis-9, trans-11 CLA was incorporated into the membrane of the culture grown in the presence of CLA (0.03 mg/ml) compared with the culture, grown in the absence of CLA, which contained no CLA (FIG. 12.). The trans-9, trans-11-CLA as observed in the supernatant was also present in the membrane following incubation with cis-9, trans-11 CLA (0.012 mg/ml). Clearly the bacterial cell has the capacity to convert cis-9, trans-11 CLA to trans-9, trans-11-CLA. An increase of 54.8% in the cis-9-C 18:1 oleic acid membrane content was obtained following incubation of B.breve 2258 in CLA (0.5 mg/ml). This amount of oleic acid in the membranes, formed relative to the control, was greater in the LA treated cells (2.7-fold increase) than the CLA treated cells. As observed in the cell membranes obtained following incubation of B.breve 2258 in LA (0.5 mg/ml), the trans-11-C 18:1 vaccenic acid content of membranes was lower in the cells incubated with cis-9, trans-11 CLA than the control pellets (5.8-fold greater in the control). Only a very small increase was obtained in the content of C 18:0 stearic acid in the membranes of CLA treated cells compared with controls.

The GLC analysis confirmed that B.breve 2258 converted LA to CLA and that a significant amount trans-9, trans-11-CLA was also formed and the data also indicates that a further biohydrogenation of cis-9, trans-11 CLA to C 18:1 isomers, preferably the cis-9-C 18:1 isomer occurs as a result of incubation with *B.breve* 2258 strain. Since also a small increase of C 18:0 was detected in the chromatogram, it is possible that additional enzymes are involved, but whether this activity is significant is unclear. The increase in saturation was obtained in both the supernatant and the bacterial pellets. Also when the pure CLA isomer was incubated with *B. breve* 2258 it was further hydrogenated to more saturated fatty acids, primarily cis-9-C 18:1. This may support the theory that incorporation of a trans fatty acids instead of cis, and saturation or trans conversion, of cis double bonds is a strategy for the bacterial cell to counteract for the increased fluidity that occurs when LA and the cis-9, trans-11 CLA isomer (which has a cis bond) is interfering with the membranes which leads to expansion of membrane, elevation of membrane permeability and impairment of membrane functions (Junkers and Ramos, 1999; Weber et al., 1994).

Interestingly in this study, the differences in fatty acid composition when adding LA and CLA respectively, to the supernatant and pellets, is not very significant. When adding the pure cis-9, trans-11 CLA isomer to the supernatant it is converted to a great extent to other CLA isomer, which is not the case in the LA added supernatant.

Because of all the beneficial health effects of CLA, the ability of strains of *bifidobacteria*, natural inhabitants of the intestine, to convert free linoleic acid to CLA can be considered as a novel probiotic trait. Indeed, it is tempting to suggest that the anticarcinogenic activity ascribed to some of these probiotic bacteria could be linked to their ability to produce CLA. Development of probiotic dairy products with elevated CLA levels also provides an exciting opportunity. Exploitation of probiotic *bifidobacteria* harbouring CLA biosynthetic capabilities offers novel opportunities in the rational design of improved health-promoting functional foods, with the benefits of enriched CLA and probiotic bacteria.

REFERENCES

Banni S., Angioni E., Casu V., Melis M. P., Carta G., Corongiu F. P., Thompson H., Ip C. Decrease in linoleic acid metabolites as a potential mechanism in cancer risk reduction by conjugated linoleic acid. *Carcinogenesis* 20(6): 1019–1024 (1999).

Belury M. A. Conjugated dienoic linoleate: A polyunsaturated fatty acid with unique chemoprotective properties. *Nutrition Reviews* Vol 53, No 4: 83–93 (1995).

Bergeÿs Manual of Systematic Bcateridlogy Vol III (1989).

Brock T. D., Madigan M. T., Martinko J. M., Parker J. Biology of Microorganisms, 7$^{th}$ ed. Prentice-Hall International, London, (1994).

Chin S. F., Liu W., Storkson J. M., Ha Y. L. and Pariza M. W. Dietary sources of conjugated dienoic isomeres of linoleic acid, a newly recognized class of anticarcinogens. *J. Food Comp. and Anal.* 5: 185–197 (1992).

Chin Sou F., Storkson Jayne M., Liu W. Albright Karen J., Pariza Michael W. Conjugated linoleic acid (9,11- and 10,12-octadecadienoic acid) is produced by conventional but not germ free rats fed linoleic acid. *J. Nutr.* 124: 694–701 (1993).

Cook Mark E. and Pariza Michael. The role of conjugated linoleic acid (CLA) in health. *Int Dairy journal*, 8: 459–462 (1998).

Cook M. E., Jerome D. L., Pariza M. W. Broilers fed conjugated linolec acid had enhanced bone ash. *Poultry Science* 76: S41 (1997).

Doyle Ellin. Scientific forum explores CLA knowledge. *INFORM* 9:69–73 (1998).

Fritsche J., Mossoba M. M., Yurawecz M. P., et al. Conjugated linoleic acid (CLA) isomers in human adipose tissue. *Zeit-schrift Lebensmittel. Untersuchung Forscung A-Food Research & Technology* 205:415–418 (1997).

Fritsche Jan and Steinhart Hans. Amounts of conjugated linoleic acid (CLA) in German foods and evaluation of daily intake. *Z Lebensm Unters Forsch A* 206: 77–82 (1998).

Fritsche Jan and Steinhart Hans. Analysis, occurence and physiological properties of trans fatty acids (TFA) with particlar emphasis on conjugated linoleic acid isomers (CLA)-a review. *Lipid*, 6S: 190–210 (1998).

Fujimoto K., Kimoto H., Shishikura M., Endo Y., Ogimoto K. Bio-hydrogenation of linoleic acid by anaerobic bacteria isolated from rumen. *Biosci. Biotech. Biochem.* 57(6):1026–1027 (1993).

Goldin Barry R. Health benefits of probiotics. *British Journal of Nutrition*, 80: 293–207 (1998).

Ha Y. L., Grimm N. K. and Pariza M. W. Anticarcinogens from fried ground beef: heat altered derivatives of linoleic acid. *Carcinogenesis* 8:1881–1887 (1987).

Ha Y. L., Storkson J, Pariza M. W. Inhibition of benzo (a)pyrene-induced neoplasia by conjugated dienoic derivatives of linoleic acid. *Cancer Res.* 50:1097–1101 (1990).

Herbel Barbara K., McGuire Michelle K., McGuire Mark A., Schultz Terry D. Safflower oil consumption does not increase plasma conjugated linoleic acid concentrations in humans. *Am. J. Clin. Nutr.* 67: 332–337 (1998).

Huang Y. C., Luedecke L. O., Schultz T. D. Effect of Cheddar-cheese consumption on the plasma conjugated linoleic acid concentration in men. *Nutr. Res.* 14:373–386 (1994).

Hughes Peter E., Hunter William J., Tove Samuel B. Biohydrogenation of unsaturated fatty acids. *The Journal of Biological Chemistry* Vol. 257 No 7: 3643–3649 (1982).

Ip C, Chin S. F, Scimeca J. A, Pariza M. W. Mammary cancer prevention by conjugated dienoic derivatives of linoleic acid. *Cancer Res.* 51:6118–6124 (1991).

Ip C., Singh M., Thompson H. J. Cojugated linoleic acid supresses mammary *carcinogenesis* and proliferative activity of the mammary gland in the rat. *Cancer Res.* 54: 1212–1215 (1994).

Ip C, Scimeca J. A., Thompson H. J. Effect of timing and duration of dietary conjugated linoleic acid on mammary cancer supression. *Nutr. Cancer* 24:241–247 (1995).

Ip C, Jiang C., Thompson H. J. Scimeca J. A. Retention of conjugated linoleic acid in the mammary gland is associated with tumour inhibition during the post— initiation phase of *carcinogenesis. Carcinogenesis* 18:755–759 (1997).

Jiang Jin, Björk Lennart, Fondén Ragne. Production of conjugated linoleic acid by dairy starter cultures. *J. Appl. Microbiol.* 85:95–102 (1998).

Jiang J., Wolk A., Vessby B. Relation between the intake of milk fat and the occurence of conjugated linoleic acid in human adipose tissue. *Am. J. Clin. Nutr.* 70:21–29 (1999).

Kepler C. R., Tove S. B. Linoleate @$^{12}$-cis @$^{11}$-trans-Isomerase. *Methods in enzymology* Vol XIV p. 105 (1969).

Kepler C. R., Tucker W. P., Tove S. B. Biohydrogenation of unsaturated fatty acids. *The Journal of Biological Chemistry* Vol. 246 No 14: 3612–3620 (1970).

Kepler C. R., Tucker W. P., Tove S. B. Biohydrogenation of unsaturated fatty acids. *The Journal of Biological Chemistry* Vol. 246, No 9: 2765–2771 (1971).

Knekt P., Järvinen R., Seppänen R., Pukkala E., Aromaa A. Intake of daily products and risk of brest acncer. *Br. J. Cancer* 73:687–691.

Kun Lee Yuan and Salminen Seppo. The coming of age of probiotics. *Trends in Food Science & Technology*, 6: 241–245 (1995).

Lal D., Narayanan K. M. Effect of lactation number on the polyunsaturated fatty acids and and oxidative stbility of milk fats. *Indian J. Dairy Sci* 37:225–229 (1984).

Lawless F., J. J. Murphy., D Harrington., R. Devery., C. Stanton. Elevation of conjugated cis-9, trans-11-octa-decadienoic acid in bovine milk because of dietary supplementation. *J. Dairy Sci.* 81:3259–3267 (1998).

Lee K. Y., Salminen S. The coming of age of probiotics. *Trends Food Sci. & Tech.* &: 241–245 (1995).

Lee K. N., Kritchevsky D., Pariza M. W. Conjugated linoleic acid and *atherosclerosis* in rabbits. *Atherosclerosis* 108:19–25 (1994).

Liew C., Schut H. A. J., Chin S. F., Pariza M. W., Dashwood R. H. Protection of conjugated linoleic acid against2-amino-3-methylimidazo(4,5-f) quinoline induced colon *carcinogenesis* in the F344 rat—a study of inhibitory mechanisms. *Carcinogenesis* 16:3037–3043 (1995).

Lin H., Boylston T. D., Chang M. J., Luedecke L. O., Schultz T. D. Survey of the conjugated linoleic acid contenets of dairy products. *J. Dairy Sci.* 78:2358–2365 (1995).

Malik A. C., Reinbold G. W., Vedamuthu E. R. An evaluation of the taxonomy of *Propionibacterium*. *Canadian J. Microbiology* 14:1185–1191 (1968).

Miller C. C., Park Y., Pariza M. W., Cook M. E. Feeding conjugated linoleic acid to animals partially overcomes catabolic responses due to endotoxin injection. *Biochem. Biophys. Res. Commun.* 198:1107–1112 (1994).

Munday John S., Thompson Keith G., James Kerry A. C. Dietary conjugated linoleic acids promote fatty streak formation in the C57BL/6 mouse *atherosclerosis* model. *Br. J. Nutr.* 81:251–255 (1999).

Naidu A. S., Bidlack W. R., Clemens R. A., Probiotic spectra of lactic acid bacteria (LAB). *Crit. Rev. Food Sci. Nutr.* 39(1):13–126 (1999).

Nicolosi R. J., Rogers E, J., Kritchevsky D., Scimeca J. A., Huth P. J. Dietary conjugated linoleic acid reduces plasma lipoproteins and early aortic *atherosclerosis* in hyper-chloesterolemic hamsters. *Artery* 22:266–277 (1997).

Pariza M. W. Animal studies: summary, gaps and future research. *Am. J. Clin. Nutr.* 66:S1539–1540 (1997).

Rudel L. L. Invited commentary. Atherosclerosis and conjugated linoleic. acid. *Br. J. Nutr.* 81:177–179 (1999).

Salminen Irma, Mutanen Marja, Jauhiainen Matti, Aro Antti. Dietary trans fatty acids increase conjugated linoleic acid levels in human serum. *Nutritional Biochemistry* 9: 93–98 (1998).

Sanders M. E. Development of consumer probiotics for the US market. *Br. J. Nutr.* 80(4):S213–218 (1998).

Schonberg S., Krokan H. E. The inhibitory effect of conjugated dienoic derivatives (cla) of linoleic acid on the growth of human tumour cell lines is in part due to increased lipid peroxidation. *Anticancer Res.* 15:1241–1246 (1995).

Schultz T. D., Chew B. P., Seaman W. R. Differential stimulatorry and inhibitory responses of human mcf-7 breast cancer cells to linoleic acid and conjugated linoleic acid in culture. *Anticancer Res.* 12:2143–2145 (1992).

Sehat Najibullah, Yurawecz Martin P., Roach John A. G., Mossoba Magdi M, Kramer John K. G. and Ku Youh. Silver ion high performance liquid chromatographic separation and identification of conjugated dienoic linoleic acid isomers. *Lipids* 33: 217–221 (1998).

Shantha N. C., Moody W. G., Tabeidi Z. Conjugated linoleic acid concentrationsin dairy products as affected by processing and storage. *J. Food Sci* 60(4):695–697 (1995).

Stanton C., Lawless F., Kjellmer G., Harrington D., Devery R., Conolly J. F., Murphy J: J. Dietary influences on bovine milk cis-9, trans-11-conjugated linoleic acid content. *J. Food Sci.* 62:1083–1086 (1997).

Tomatori M. *Bifidobacteria* and their role in human health. *J. Industrial Microbiology* 6:263–268 (1993).

Van Nostrand R., Douglas M., Considine P. E. Scientific Encyclopedia 7$^{th}$ ed. Vol II (1989).

Visonneau S., Cesano A., Tepper S. A., Scimeca J. A., Santoli D., Kritchevsky D. Conjugated linoleic acid supresses the growth of human breast adenocarcinoma cells in scid mice. *Anticancer Res.* 17:969–973 (1997).

Yang X., Pariza M. W. Conjugated linoleic acid (CLA)-producing bacteria: isolation, identification and properties of their linoleic acid isomerases. *IFT Annual Meeting* p. 243 (1995).

Jay, James M., Modern Food Microbiology, 5$^{th}$ ed. Chapman and Hall (1996)

Cogan, T M. and Accolas, J.-P., Dairy Starter Cultures. VCH Publishers, Inc. (1996).

Moore, T. Spectroscopic Changes in Fatty Acids. VI. General, *Biochem. J.* 33, 1635–1638 (1939)

Booth et al. A Study of Seasonal Variation in Butter Fat. II. A Seasonal Spectroscopic Variation in the Fatty Acid Fraction, *Bioch. J.* 29, 133–137 (1935).

Michelle K. McGuire, Mark A. McGuire, Kristin Ritzenthaler, Terry D. Schultz. Dietary Sources and Intakes of Conjugated Linoleic Acid Intake in Humans. Advances in Conjugated Linoleic Acid Research, Volume 1(1999).

Fritsche, Jan and Steinhart, Hans. Amounts of Conjugated Linoleic Acid (CLA) in German Foods and Evaluation of Daily Intake. *Z Leberuuusm Unters Forsch A* 206: 77–82 (1998).

Chin, S. F., Liu, W., Storkson, j. M., Ha, Y. L., Pariza, M. W. Dietary Sources of Conjugated Dienoic Isomers of Linoleic Acid, a newly recognized class of *anticarcinogens*. *J. Food Comp. And Anal.* 5: 185–197 (1992).

Nordgren, Maria. Microbial Biosynthesis by Human Probiotic Strains (1999).

Jiang, Jin. Conjugated Linoleic Acid. Occurrence, Oxidation and Production by Dairy Starter Cultures (1998).

Hoffman and Winston, Gene 1987, vol 57, p 267–272 (1987).

Altschul, S. F., Gish, W., Miller, W., Myers, E. W. & Lipman, D. J. (1990) "Basic local alignment search tool." J. Mol. Biol. 215:403–410. Medline Junker, Frank and Ramos, Juan L (1999). Involvment of the cis/trans Isomerase Cti in Solvent Resistance of *Pseudomonas putida* DOT-T1E. Journal of Bacteriology, September 1999, p 5693–5700.

Weber, Frans J, Isken, Sonja, de Bont, Jan A. M., (1994). Cis/trans isomerization of fatty acids as a defence mechanism of *Pseudomonas putida* strains to toxic concentrations of toluene. Microbiology (1994), 140, 2013–2017.

Ha, Y. L., Grimm, N. K. and Pariza, M. W. (1987). *Anticarcinogens* from fried ground beef: heat-altered derivatives of linoleic acid. *Carcinogenesis* 8, 1881–1887.

Rosson, Reinhardt, A.; Grund, Alan, D.; Deng, Mind-De; Sanchez-Riera, Fernando. (1999). Linoleate Isomerase. Patent. WO 99/32604.

We claim:

1. An isolated nucleic acid molecule which encodes a polypeptide with conjugated linoleic acid isomerase activity, or the full complement thereof, selected from the group consisting of:
   a) a nucleic acid molecule comprising the nucleotide sequence set forth in SEQ ID NO: 1,
   b) a nucleic acid molecule comprising a nucleotide sequence which encodes a polypeptide sequence comprising the amino acid sequence as set forth in SEQ ID NO:2,
   c) a nucleic acid molecule comprising a nucleotide sequence which is a derivative of the nucleic acid sequence shown in SEQ ID NO: 1, which encodes a polypeptide having at least 98% identity to the entire amino acid sequence as set forth in SEQ ID NO:2 without substantially reducing the enzymatic activity of the polypeptide; and
   d) a nucleic acid molecule comprising a nucleotide sequence which is at least 95% identical to the entire nucleotide sequence set forth in SEQ ID NO:1 and encodes a polypeptide having conjugated linoleic acid isomerase activity.

2. A nucleic acid construct comprising a nucleic acid molecule of claim 1, where the nucleic acid molecule is linked to one or more regulatory signals.

3. A vector comprising a nucleic acid molecule of claim 1 or the nucleic acid construct of claim 2.

4. A transgenic microorganism comprising at least one nucleic acid molecule of claim 1 or at least one nucleic acid construct of claim 2.

5. The transgenic microorganism of claim 4, which is a bacterium.

6. A process for the production of conjugated linoleic acid comprising cultivating a recombinant microorganism into which the nucleic acid molecule of claim 1 or the nucleic acid construct of claim 4 has been introduced in the presence of linoleic acid and isolating the formed conjugated linoleic acid.

7. The process of claim 6 wherein the conjugated linoleic acid is cis-9, trans-11 octadecadienoic acid.

8. The process of claim 6 wherein the microorganism is selected from the group consisting of *Bifidobacterium breve, Bifidobacterium dentium* and *Bifidobacterium pseudocatenulatum*.

9. The process of claim 6 wherein the concentration of conjugated linoleic acid in the culture medium is higher than 1 mg/ml.

10. A process for the production of conjugated linoleic acid which comprises introducing at least one nucleic acid sequence as claimed in claim 1 or at least one nucleic acid construct as claimed in claim 2 into an oil-producing organism, growing this organism, isolating the oil contained in the organism and liberating the fatty acids contained in the oil.

11. A process for the production of triglycerides with an increased content of conjugated linoleic acid, which comprises introducing at least one nucleic acid sequence as claimed in claim 1 or at least one nucleic acid construct as claimed in claim 4 into an oil-producing organism, growing this organism and isolating the oil contained in the organism.

12. The process of claim 10, wherein the organism is a microorganism.

13. The process of claim 10, wherein the organism is a microorganism of the genera *Bifidobacterium, Propionibacterium, Lactobacillus* or *Butyrivibrio*.

14. The process of claim 10, wherein the organism is a microorganism of the genus *Bifidobacterium*.

15. The process of claim 6, wherein the microorganism is of the genus *Bifidobacterium*.

16. The process of claim 7 wherein the microorganism is selected from the group consisting of *Bifidobacterium breve, Bifidobacterium dentium* and *Bifidobacterium pseudocatenulatum*.

17. The process of claim 7 wherein the concentration of conjugated linoleic acid in the culture medium is higher than 1 mg/ml.

* * * * *

UNITED STATES PATENT AND TRADEMARK OFFICE
CERTIFICATE OF CORRECTION

| | | |
|---|---|---|
| PATENT NO. | : 7,223,543 B2 | Page 1 of 1 |
| APPLICATION NO. | : 10/480121 | |
| DATED | : May 29, 2007 | |
| INVENTOR(S) | : Catherine Stanton et al. | |

It is certified that error appears in the above-identified patent and that said Letters Patent is hereby corrected as shown below:

In Claim 6, at column 41, line 49, replace "claim 4" with --claim 2-- so it should correctly appear as --nucleic acid construct of claim 2--.

In Claim 11, at column 42, line 32, replace "claim 4" with --claim 2-- so it should correctly appear as --nucleic acid construct as claimed in claim 2--.

Signed and Sealed this

Twenty-second Day of July, 2008

JON W. DUDAS
*Director of the United States Patent and Trademark Office*